US007977098B2

(12) United States Patent
Jiang et al.

(10) Patent No.: US 7,977,098 B2
(45) Date of Patent: Jul. 12, 2011

(54) ANTIGENIC BINDING PATTERNS OF NOROVIRUS TO HUMAN HISTO-BLOOD GROUP ANTIGENS

(75) Inventors: Xi Jiang, Cincinnati, OH (US); Jacques Le Pendu, Nantes (FR)

(73) Assignees: Children's Hospital Medical Center, Cincinnati, OH (US); INSERM, Nantes Codex (FR)

( * ) Notice: Subject to any disclaimer, the term of this patent is extended or adjusted under 35 U.S.C. 154(b) by 86 days.

(21) Appl. No.: 11/264,992

(22) Filed: Nov. 2, 2005

(65) Prior Publication Data

US 2006/0115846 A1    Jun. 1, 2006

Related U.S. Application Data

(63) Continuation-in-part of application No. 10/520,087, filed as application No. PCT/US03/17247 on Jun. 2, 2003.

(60) Provisional application No. 60/385,283, filed on May 31, 2002, provisional application No. 60/385,296, filed on May 31, 2002.

(51) Int. Cl.
*C12Q 1/70* (2006.01)
*G01N 33/53* (2006.01)
(52) U.S. Cl. .................. 435/975; 435/5; 424/216.1
(58) Field of Classification Search ................. 435/975, 435/5, 7.1, 7.93, 7.94
See application file for complete search history.

(56) References Cited

U.S. PATENT DOCUMENTS

| | | | |
|---|---|---|---|
| 4,916,213 A | 4/1990 | Scannon et al. | |
| 5,254,342 A | 10/1993 | Shen et al. | |
| 5,326,857 A | 7/1994 | Yamamoto et al. | |
| 5,338,689 A * | 8/1994 | Yves et al. | 436/518 |
| 5,559,014 A | 9/1996 | Estes et al. | |
| 5,589,453 A | 12/1996 | Greve | |
| 5,643,579 A | 7/1997 | Hung et al. | |
| 5,665,534 A | 9/1997 | Vandenbergh et al. | |
| 5,750,394 A | 5/1998 | Palese et al. | |
| 5,783,193 A | 7/1998 | Michael et al. | |
| 5,786,340 A | 7/1998 | Henning et al. | |
| 5,789,230 A | 8/1998 | Cotten et al. | |
| 5,861,241 A | 1/1999 | Herrmann et al. | |
| 6,045,854 A | 4/2000 | Prieto et al. | |
| 6,130,205 A | 10/2000 | Stapleton et al. | |
| 6,140,043 A | 10/2000 | Dierich et al. | |
| 6,156,883 A | 12/2000 | Estes et al. | |
| 6,187,762 B1 | 2/2001 | Mandeville, III et al. | |
| 6,254,867 B1 | 7/2001 | Reisner et al. | |
| 6,258,789 B1 | 7/2001 | German et al. | |
| 6,300,090 B1 | 10/2001 | Steinman et al. | |
| 2002/0019991 A1 | 2/2002 | Prieto et al. | |

OTHER PUBLICATIONS http://acronyms.thefreedictionary.com/kit, search on Feb. 18, 2008, p. 1.*
http://encyclopedia.thefreedictionary.com/assay, searched on Feb. 18, 2008, p. 1.*
Immuncor Inc. manufacture Advertisement published by Immucor Websit , search by Sep. 2008.*
Eldon Biologicals A/S, Eldoncar Home Kit 2511 manufcature catolog published on web site, searched on Sep. 2008.*
Evaluation Report for Eldon Biologicals A/S published 2004.*
Eldon Biologicals A/S, Eldoncar Home Kit 2511 manufcature protocol published on web site, searched on Sep. 2008.*
EldonCard Home Blood Testing kit published on Website, search on Sep. 2008.*
Jiang et al. JID, 2004, Nov. 15, vol. 190, pp. 1850-1859.*
Oriol. et al. Am. J. Hum, Genet, 1981, vol. 33, pp. 551-560.*
WorlReferecne.com English Dictionary, searched on Jan. 16, 2010.*
Guix et al. J. Virol. 2007, vol. 81, No. 22, pp. 12238-12248.*
Burton-Macleod, Jonathan A. et al., Evaluation and Comparison of Two Commercial Enzyme-Linked Immunosorbent Assay Kits for Detection of Antigenically Diverse Human Noroviruses in Stool Samples, *Journal of Clinical Microbiology*, Jun. 2004, vol. 42, No. 6, pp. 2587-2595.
Huang, Pengwei et al., Norovirus and Histo-Blood Group Antigens: Demonstration of a Wide Spectrum of Strain Specificities and Classification of Two Major Binding Groups among Multiple Binding Patterns, *Journal of Virology*, Jun. 2005, vol. 79, No. 11, pp. 6714-6722.
Jiang, Xi et al., Human Milk Contains Elements That Block Binding of Noroviruses to Human Histo-Blood Group Antigens in Saliva, *The Journal of Infectious Diseases*, Nov. 15, 2004, vol. 190, pp. 1850-1859 (electronically published Oct. 11, 2004).
Tan, Ming et al., Norovirus and its histo-blood group antigen receptors: an answer to a historical puzzle, *Trends in Microbiology*, Jun. 6, 2005, vol. 13, No. 6, pp. 285-293 (Available online Apr. 30, 2005).
Tan, Ming et al., The P Domain of Norovirus Capsid Protein Forms a Subviral Particle That Binds to Histo-Blood Group Antigen Receptors, *Journal of Virology*, Nov. 2005, vol. 79, No. 22, pp. 14017-14030.
Farkas T. et al., Molecular Detection and Sequence Analysis of Human Caliciviruses . . . , Journal of Medical Virology, Jan. 2002, vol. 67, pp. 567-573.
Farkas T. et al., Homologous versus Heterologous Immune Responses to Norwalk-Like Viruses . . . , The Journal of Infectious Diseases, Jan. 2003, vol. 187, pp. 187-193.

(Continued)

*Primary Examiner* — Bao Li
(74) *Attorney, Agent, or Firm* — Hasse & Nesbitt LLC; Daniel F. Nesbitt

(57) ABSTRACT

The invention provides a compound which competitively inhibits the binding of a norovirus with a native blood antigen of a human host, as well as a kit for determining whether an individual has been infected by a norovirus. Also provided is a method for determining the susceptibility of an individual to infection by a particular, known strain of norovirus. The invention is based on the determination that noroviruses recognize human blood antigens such as human histo-blood group antigens (HBGAs) as a receptor in seven specific binding patterns. The invention allows one to predict that a particular strain of norovirus can infect humans who have a particular human histo-blood type, as well as blood antigens that can bind the particular strain of infecting norovirus. The invention also allows one to predict that a particular strain of norovirus will bind with one or more particular histo-blood group antigens, but will not bind with other blood group antigens.

17 Claims, 9 Drawing Sheets

OTHER PUBLICATIONS

Green K.Y. et al., Taxonomy of Caliciviruses, The Journal of Infectious Diseases, 2000, vol. 181(Suppl 2), pp. S322-S330.

Hale A.D. et al., Expression and Self-Assembly of Grimsby Virus . . . , Clinical and Diagnostic Laboratory Immunology, Jan. 1999, vol. 6, No. 1, pp. 142-145.

Harrington P.R. et al., Binding of Norwalk Virus-Like Particles . . . , Journal of Virology, Dec. 2002, vol. 76, No. 23, pp. 12335-12343.

Harrington P.R. et al., Norovirus Capture with Histo-Blood Group Antigens . . . , Journal of Virology, Mar. 2004, vol. 78, No. 6, pp. 3035-3045.

Hennessy E.P. et al., Norwalk Virus Infection and Disease . . . , The Journal of Infectious Diseases, 2003, vol. 188, pp. 176-177.

Huang P. et al., Noroviruses Bind to Human ABO, Lewis, and Secretor . . . , The Journal of Infectious Diseases, 2003, vol. 188, pp. 19-31.

Hutson A.M. et al., Norwalk Virus-Like Particle Hemagglutination . . . , Journal of Virology, Jan. 2003, vol. 77, No. 1, pp. 405-415.

Jiang X. et al., Expression, Self-Assembly, and Antigenicity of a Snow Mountain Agent . . . , Journal of Clinical Microbiology, Jun. 1995, vol. 33, No. 6, pp. 1452-1455.

Jiang X. et al., Expression, Self-Assembly, and Antigenicity of the Norwalk Virus Capsid Protein, Journal of Virology, Nov. 1992, vol. 66, No. 11, pp. 6527-6532.

Jiang X. et al., Baculovirus expression and antigenic characterization of the capsid proteins of three Norwalk-like . . . , Archives of Virology, 2002, vol. 147, pp. 119-130.

Kumar S. et al., MEGA2: molecular evolutionary genetics analysis software, Bioinformatics Applications Note, 2001, vol. 17, No. 12, pp. 1244-1245.

Lew J.F. et al., Molecular Characterization of Hawaii Virus and Other Norwalk-like Viruses . . . , The Journal of Infectious Diseases, Mar. 1994, vol. 170, pp. 535-542.

Lindesmith L. et al., Human susceptibility and resistance to Norwalk Virus infection, Nature Medicine, May 2003, vol. 9, No. 5, pp. 548-553.

Nicholas K. B. et al., GeneDoc: Analysis and Visualization of Genetic Variation, http://www.psc.edu/biomed/genedoc/ebinet.htm.

Tan M. et al., The P Domain of Norovirus Capsid Proten Forms Dimer and Binds . . . , Journal of Virology, Jun. 2004, vol. 78, No. 12, pp. 6233-6242.

Tan M. et al., Mutations within the P2 Domain of Norovirus Capsid Affect Binding . . . , Journal of Virology, Dec. 2003, vol. 77, No. 23, pp. 12562-12571.

Tan M. et al., *E. coli*-Expressed Recombinant Norovirus Capsid Proteins Maintain Authentic Antigenicity . . . , Journal of Medical Virology, 2004, vol. 74, pp. 641-649.

Wobus C. E. et al., Replication of Norovirus in Cell Culture Reveals a Tropism for Dendritic Cells and Macrophages, PLoS Biology, Dec. 2004, vol. 2, issue 12, pp. 0001-0009.

Brinker, James P et al., Immunoglobulin M. Antibody Test to Detect Genogroup II Norwalk-Like Virus Infection, Journal for Clinical Microbiology, Sep. 1999, vol. 37, No. 9, p. 2983-2986.

Erdman, Dean D. et al., Serum Immunoglobulin A Response to Norwalk Virus Infection, Journal of Clinical Microbiology, Jun. 1989, vol. 27 No. 6, p. 1417-1418.

Gray, J.J. et al., Prevalence of Antibodies to Norwalk Virus in England: Detection by Enzyme-Linked Immunosorbent Assay Using Baculovirus-Expressed Norwalk Virus Capsid Antigen, Journal of Clinical Microbiology, Apr. 1993, vol. 31 No. 4, p. 1022-1025.

Hale, Anthony D. et al., Identification of an Epitope Common to Genogroup 1 "Norwalk-Like Viruses", Journal of Clinical Microbiology, Apr. 2000, vol. 38, No. 4, p. 1656-1660.

Hutson, Anne M. et al., Norwalk Virus Infection and Disease is Associated with ABO Histo-Blood Group Type, The Journal of Infectious Diseases, 2002;185, p. 1335-7.

Hutson, Anne M. et al., ABO Phenotype Association with Norwalk Virus Infection and Disease may be Related to Norwalk Virus-Like Particle Binding H Antigens; Gastroenterology, vol. 122, No. 4 Suppl. 1, Apr. 2002, pp. A-141, XP009054158 & Digestive Disease Week and the 103$^{rd}$ Annual Meeting of the American Gastroenterological Association; San Francisco, CA, USA; May 19-22, 2002, abstract.

Jiang, Xi et al., Norwalk Virus Genome Cloning and Characterization, Science, Dec. 14, 1990, vol. 250, p. 1580-1583.

Jiang, Xi et al., Sequence and Genomic Organization of Norwalk Virus, Virology (1993), 195, p. 51-61.

Marionneau, S. et al., ABH and Lewis Histo-Blood Group Antigens, A Model for the Meaning of Oligosaccharide Diversity in the Face of a Changing World, Biochimie Jul. 2001, 83(7):565-73.

Marionneau, Severine et al., Norwalk Virus Binds to Histo-Blood Group Antigens Present on Gastroduodenal Epithelial Cells of Secretor Individuals, Gastroenterology Jun. 2002;122 p. 1967-1977.

Pelosi, Emanuela et al., The Seroepidemiology of Genogroup 1 and Genogroup 2 Norwalk-Like Viruses in Italy, Journal of Medical Virology, Apr. 1, 1999, vol. 58, Issue 1, p. 93-99, abstract.

Prasad, B.V. Venkataram et al., X-Ray Crystallographic Structure of the Norwalk Virus Capsid, Science, Oct. 8, 1999, vol. 286, p. 287-290.

Tamura, Masaru et al., Interaction of Recombinant Norwalk Virus Particles with the 105-Kilodalton Cellular Binding Protein, a Candidate Receptor Molecule for Virus Attachment, Journal of Virology, Dec. 2000, vol. 74, No. 24, p. 11589-11597.

Treanor, J. J. et al., Development of an Enzyme Immunoassay for the Hawaii Agent of Viral Gastroenteritis, Journal of Virol Methods Dec. 1988; 22(2-3):207-14.

White, Laura J. et al., Attachment and Entry of Recombinant Norwalk Virus Capsids to Cultured Human and Animal Cell Lines, Journal of Virology, Oct. 1996, vol. 70, No. 10, p. 6589-6597.

"Sixth International Symposium" on Positive Strand RNA Viruses (May 28-Jun. 2, 2001), Institut Pasteur, Paris, France; Scientific Program Abstracts "Norwalk Virus Binds to H Type 1 Histro-Blood Group Antigen Present on Gastro-Duodenal Epithelial Cells of "Secretor" Phenotype Individuals", abstract (2 pages).

Adler, P. et al, High Affinity Binding of the *Entamoeba histolytica* Lectin to Polyvalent *N*-Acetylgalactosaminides, *The Journal of Biological Chemistry*, Mar. 10, 1995; vol. 270, No. 10, p. 5164-5171.

Atmar, R. et al., Diagnosis of Noncultivatable Gastroenteritis Viruses, the Human Caliciviruses, Clinical Microbiology Reviews, Jan. 2001, vol. 14, No. 1, pp. 15-37, (23 pages).

Estes, M. et al., Norwalk Virus Vaccines: Challenges and Progress, The Journal of Infectious Diseases, May 2000, 181(Suppl 2), pp. S367-S373, (Cover, 1 page—Article, 7 pages).

Pelosi, E. et al., The Seroepidemiology of Genogroup 1 and Genogroup 2 Norwalk-like Viruses in Italy, Journal of Medical Virology, Apr. 1, 1999, vol. 58, Issue 1, pp. 93-99, (7 pages).

"Sixth International Symposium" on Positive Strand RNA Viruses (May 29, 2001), Institut Pasteur, Paris, France; Scientific Program Abstracts "Norwalk Virus Binds to H Type 1 Histo-Blood Group Antigen Present on Gastro-Duodenal Epithelial Cells of "Secretor" Phenotype Individuals", abstract (2 pages).

\* cited by examiner

ANTIGENIC BINDING PATTERNS OF NOROVIRUS TO HUMAN HISTO-BLOOD GROUP ANTIGENS

CROSS-REFERENCE TO RELATED APPLICATIONS

This application is a continuation-in-part of application Ser. No. 10/520,087, filed Dec. 28, 2004, which is the National Stage of International Application No. PCT/US03/17247, filed Jun. 2, 2003, which claims the benefit of U.S. Provisional Application No. 60/385,283, filed May 31, 2002 and U.S. Provisional Application No. 60/385,296, filed May 31, 2002.

INTERESTS

This invention was made with Government support by the U.S. National Institutes of Health (National Institute of Allergy and Infectious Diseases, grant RO1 AI37093, and National Institute of Child Health and Human Development, grant HD13021). The Government has certain rights in this invention.

FIELD OF THE INVENTION

The present invention relates in general to noroviruses, a.k.a. Norwalk-Like Viruses. More specifically, the invention relates to the recognition of and binding of norovirus to human histo-blood group antigens in various differing binding patterns.

BACKGROUND OF THE INVENTION

Noroviruses, previously called Norwalk-Like Viruses (NLV), are small round viruses within the calicivirus family and are important viral pathogens that cause acute gastroenteritis, the second most common illness in the United States. Norwalk disease is a mild to moderate illness that develops 1-2 days after infection by person-to-person transmission, surface contamination, or by contaminated food or water and the illness lasts for 24-60 hours. Symptoms include nausea, vomiting, diarrhea, abdominal pain and upon occasion headache and low fever. Severe illness requiring hospitalization is most unusual. Particularly large epidemic outbreaks of illness have occurred following consumption of contaminated water or uncooked food such as salad and ham, and shellfish including clams, cockles, and oysters.

Since the molecular cloning of noroviruses and the subsequent development of new diagnostic assays, noroviruses have been recognized as the most important cause of non-bacterial epidemics of acute gastroenteritis in both developed and developing countries, affecting individuals of all ages. Over 90% of non-bacterial gastroenteritis outbreaks in the United States are found to be associated with noroviruses. The percentage of individuals in developing countries who have antibodies against noroviruses at an early age is very high (as it is with poliovirus and other viruses transmitted by fecal contamination of water and foods). In the United States the percentage increases gradually with age, reaching 50% in people over 18 years of age. The antibody prevalence to noroviruses is estimated to be higher based on the data using new diagnostic methods than previously reported using old methods. Immunity, however, is not permanent, and re-infection can occur.

Although the Norwalk Virus (NV), the prototype norovirus strain, was discovered in 1972, knowledge about the virus has remained limited because it has failed to grow in cell cultures and no suitable animal models have been found for virus cultivation. Human stool samples obtained from outbreaks and from human volunteer studies, therefore, are the only source of the virus. Still the concentration of the virus in stool is typically so low that virus detection with routine electron microscopy is not possible. Although limited studies on human volunteers have shown that antibody response to norovirus challenge is protective against subsequent infection, other studies have found that pre-existing antibodies against norovirus are not protective. Even more puzzling has been that some individuals with high levels of antibody against norovirus were more susceptible to the virus than individuals who did not have the antibody, and that 20-30% of individuals who did not have antibody against norovirus could not be infected by challenge with norovirus.

Before molecular cloning of NV in 1990, several methods were developed for diagnosis that included immune electron microscopy and other immunologic methods such as radio immunoassays (RIAs) or enzyme linked immunoabsorbent assays (ELISAs). Because most of these methods use reagents from infected humans that are of limited source, they are not widely used. Since the molecular cloning of NV, several methods have been developed for diagnosis, including reverse transcription-polymerase chain reaction (RT-PCR) for detection of the viral RNA and recombinant enzyme immune assay for detection of viral antigens and antibody against viral antigens. Due to the wide genetic and antigenic diversity of noroviruses, these methods encountered problems of low detection sensitivity and specificity.

Because a tissue culture model for human norovirus infection is not available, recombinant molecular approaches have been necessary to dissect their basic biological properties. The genome of NV has been cloned, sequenced, and characterized biochemically. The genome is a single-stranded, positive-sense RNA of about 7.5 kb and is organized into three open reading frames (ORF's). ORF1 encodes the non-structural proteins such as polymerase, protease and helicase. ORF2 encodes a major capsid protein, and ORF3 encodes a minor structural protein.

Noroviruses are morphologically similar but genetically and antigenically diverse viruses. Genetically, noroviruses can be divided into two main genogroups, the "Norwalk-like viruses" (NLVs) and the "Sapporo-like viruses" of human caliciviruses, a subset of Caliciviridae. Each genogroup can be further divided into genetic clusters or genotypes. The major human strains can be genetically divided into at least 15 genetic clusters. The ORF2-encoded major capsid protein self-assembles into virus-like particles (VLPs) when the recombinant capsid protein is expressed in high concentrations from recombinant baculoviruses in insect cells. Norovirus VLPs are morphologically and immunologically indistinguishable from the wild-type viruses found in human feces, and have provided the foundation for studies of assembly, attachment, and immunobiology. Moreover, they have been indispensable for the development of diagnostic immunoassays.

Despite the lack of a tissue culture system or an animal model that accurately depicts human norovirus disease, significant advances in norovirus attachment and pathogenesis research have been achieved, including the identification of particular ABH (ABO) histo-blood group antigens as putative ligands for the attachment of noroviruses to mucosal cell surfaces. These carbohydrate epitopes are present in mucosal secretions and on many tissues throughout the human body. The complexity of the ABH histo-blood group antigens is reflected in the large number of type chain branches and modifying enzymes, as well as the broad distribution of different antigens based on blood type, genetic polymorphisms, and tissue specificity.

Although the ABH antigens are typically described as blood group antigens because of their presence on red blood cells, they are also found on other tissues, and may be more appropriately termed histo-blood group antigens (HBGAs). In the blood they exist in both a cellular form on platelets and a soluble form as blood group active glycosphingolipids coupled to plasma lipoproteins. They exist as membrane antigens on such diverse cells as vascular endothelial cells and intestinal, cervical, urothelial, pulmonary and mammary epithelial cells. Soluble forms are also found in various secretions and excretions, such as saliva, milk, urine, and feces. In some tissues, their appearance is developmentally regulated. Despite their wide distribution, genetic inheritance, developmental regulation, and importance in transfusion and transplantation, their normal physiological function, if any, remains a mystery.

At least five type chains of the ABH histo-blood group antigens have been identified, which are produced and distributed in various tissue compartments in a type-specific manner. The type 1 and 3 chain molecules are the predominant ABH histo-blood group antigens on cell surfaces of the gut, which is presumed to be the site of norovirus infection. The FUT2 enzyme, an $\alpha 1,2$-fucosyltransferase, is responsible for the production of type 1 and 3 chain ABH histo-blood group antigens. Approximately 20% of Europeans and Africans express a defective form of the FUT2 enzyme and therefore do not produce type 1 or 3 chain histo-blood group antigens on cell surfaces of the gut or in mucosal secretions; this is known as the "nonsecretor" or secretor-negative phenotype.

The type 1 and 3H antigens are produced by the FUT2 enzyme in secretor-positive individuals from H precursor molecules. The A or B enzymes produced in blood type A or B individuals, respectively (or both in blood type AB individuals), further modify the H antigens along the particular type chain to produce type-specific A or B antigens. Similarly, the type 2 chain A or B antigens are produced on red blood cells, and the presence or absence of one or more of these molecules is used to determine an individual's blood type. In the type 1 chain, the FUT3 Lewis enzyme, an $\alpha 1,4$-fucosyltransferase, modifies the H type 1 precursor to produce $Le^a$ or modifies H type 1 to produce $Le^b$. Approximately 10% of Europeans lack a functional FUT3 gene product, representative of the Lewis-negative phenotype, and therefore will not produce $Le^a$ or $Le^b$ on mucosal surfaces. Secretor-positive, Lewis-positive individuals will produce $Le^b$ and relatively less $Le^a$ on cell surfaces of the gut and in mucosal secretions, whereas secretor-negative, Lewis-positive individuals will produce only $Le^a$.

Recombinant NV VLPs were first shown to attach to H types 1 and 3 epitopes on the surfaces of gastroduodenal epithelial cells from secretor-positive individuals. In addition, Norwalk VLPs attach specifically to H type 1, H type 3, and $Le^b$ carbohydrates, even in the absence of other cellular components. The significance of these in vitro findings was recently demonstrated in vivo using a human challenge model for Norwalk virus infection. This study demonstrated that secretor-negative human volunteers, who do not produce H type 1, H type 3, and/or $Le^b$ on mucosal cell surfaces, were resistant to live NV challenge. Taken together, the results of these studies suggest that H type 1, H type 3, and $Le^b$ are attachment molecules necessary for NV infectivity in the gut.

It has also been observed that VLPs of other norovirus strains exhibit different properties of attachment to ABH histo-blood group antigens in vitro, suggesting that different norovirus genotypes may utilize different mechanisms for attachment and entry in vivo and that various other host factors may play a role in susceptibility to different norovirus strains. Because VLP reagents are not available for many norovirus strains, the overall extent to which noroviruses utilize ABH histo-blood group antigens for attachment is unclear and cannot be thoroughly evaluated using previously described biochemical methods. Also, no study to date has examined and compared the ability of wild-type virus and recombinant VLPs to attach to specific ABH histo-blood group antigens.

In the present invention, a method was developed to purify noroviruses from clinical specimens and at the same time further characterize their histo-blood group antigen attachment properties. Consistent with previous observations, various norovirus strains exhibited distinct histo-blood group antigen binding patterns. Ultimately the study of noroviruses presents the need, among other things, to understand the specific mechanism for norovirus infection within the GI tract, the specific binding properties of the prototype NV with the ABO blood antigens and the Le blood antigens, the specific binding properties of the other noroviruses with the human histo-blood phenotypes and their respective blood antigens, and the compounds and compositions that are effective to inhibit binding between noroviruses and blood antigens. The ultimate goal of current norovirus research is to prevent or treat an infection by a norovirus and/or the resulting illness.

Virus like particles (VLPs) of the various noroviruses can recognize and bind to one or more human histo-blood group antigens, and human histo-blood group antigens can recognize and bind to one or more noroviruses, in varied HBGA-norovirus binding patterns. Thus, the present invention is premised on the notion that noroviruses can infect humans who have a particular human histo-blood type that presents blood antigens that can bind the particular strain of infecting norovirus, and further that a strain of norovirus will bind with one or more HBGAs, but will not bind with all other blood group antigens. It would therefore be advantageous to understand the specific binding properties of the various norovirus strains with the ABO blood antigens and the Lewis blood antigens by characterizing the norovirus strain-specificity to human HBGAs. It would also be advantageous to provide compounds and compositions that are effective to bind specific, small regions of the norovirus capsid protein, such that a kit can be developed to determine if an individual is susceptible to infection by a particular norovirus strain.

SUMMARY OF THE INVENTION

The present invention follows from the discovery that noroviruses recognize human blood antigens such as human histo-blood group antigens (HBGAs) as a receptor in seven specific Binding Patterns. The invention allows one to predict that a particular strain of norovirus can infect humans who have a particular human histo-blood type, as well as blood antigens that can bind the particular strain of infecting norovirus. The invention also allows one to predict that a particular strain of norovirus will bind with one or more particular histo-blood group antigens, but will not bind with other blood group antigens.

A first aspect of the invention relates to a pharmaceutical composition comprising at least one compound which competitively inhibits the binding of a norovirus with a native blood antigen of a human host, and optionally a pharmaceutically acceptable carrier, the at least one compound selected from the group consisting of a protein, a polypeptide, an oligosaccharide, a natural compound, a functionally equivalent molecule, and mixtures thereof, wherein the at least one compound binds to the norovirus according to one of seven specific Binding Patterns, each binding pattern corresponding with the binding specificity of the antigenic determinant of a human histo-blood group antigen.

A second aspect of the invention relates to a kit for determining whether an individual has been infected by a norovirus, comprising: a) at least one container for receiving a biological sample from an individual suspected of being infected by a norovirus, the container comprising a media having affixed at least one blood antigen selected from the group consisting of H antigen, A antigen, B antigen, $Le^b$ antigen, $Le^a$ antigen, and mixtures thereof, or a functionally equivalent molecule thereof, and capable of complexing with a norovirus; and b) an assay for the detection of a complex of the norovirus and the blood antigen, wherein the norovirus strain is selected from the group consisting of strains VA387, MOH, NV, 02-1419, VA207, GrV, Boxer, OIF, C59, PiV, HV, MxV, DSV, BUDS, VA115, and mixtures thereof.

A third aspect of the invention relates to a method of determining the susceptibility of an individual to infection by a particular, known strain of norovirus, the method comprising the steps of: a) obtaining a biological sample from the individual, the biological sample including at least one histo-blood group antigen selected from the group consisting of H antigen, A antigen, B antigen, $Le^a$ antigen, $Le^b$ antigen, and mixtures thereof; b) contacting the known norovirus strain with the biological sample, the known norovirus strain being known to have one of seven specific Binding Patterns with histo-blood group antigens; c) subsequently contacting the known norovirus strain with a standard compound that is known to bind with the known norovirus strain according to one of the seven specific Binding Patterns, the standard compound selected from the group consisting of an oligosaccharide, a protein, a polypeptide, and poly- or monoclonal antibodies; and d) determining whether the binding of the known norovirus strain with the standard compound is decreased in the presence of the biological sample, the decrease in binding being an indication that the at least one histo-blood group antigen of the biological sample competitively inhibits the binding of the known norovirus strain with the standard compound and that the individual is susceptible to infection by the norovirus.

The nature and advantages of the present invention will be more fully appreciated from the following drawings, detailed description, and appending claims.

DETAILED DESCRIPTION OF THE INVENTION

Figure 1A:
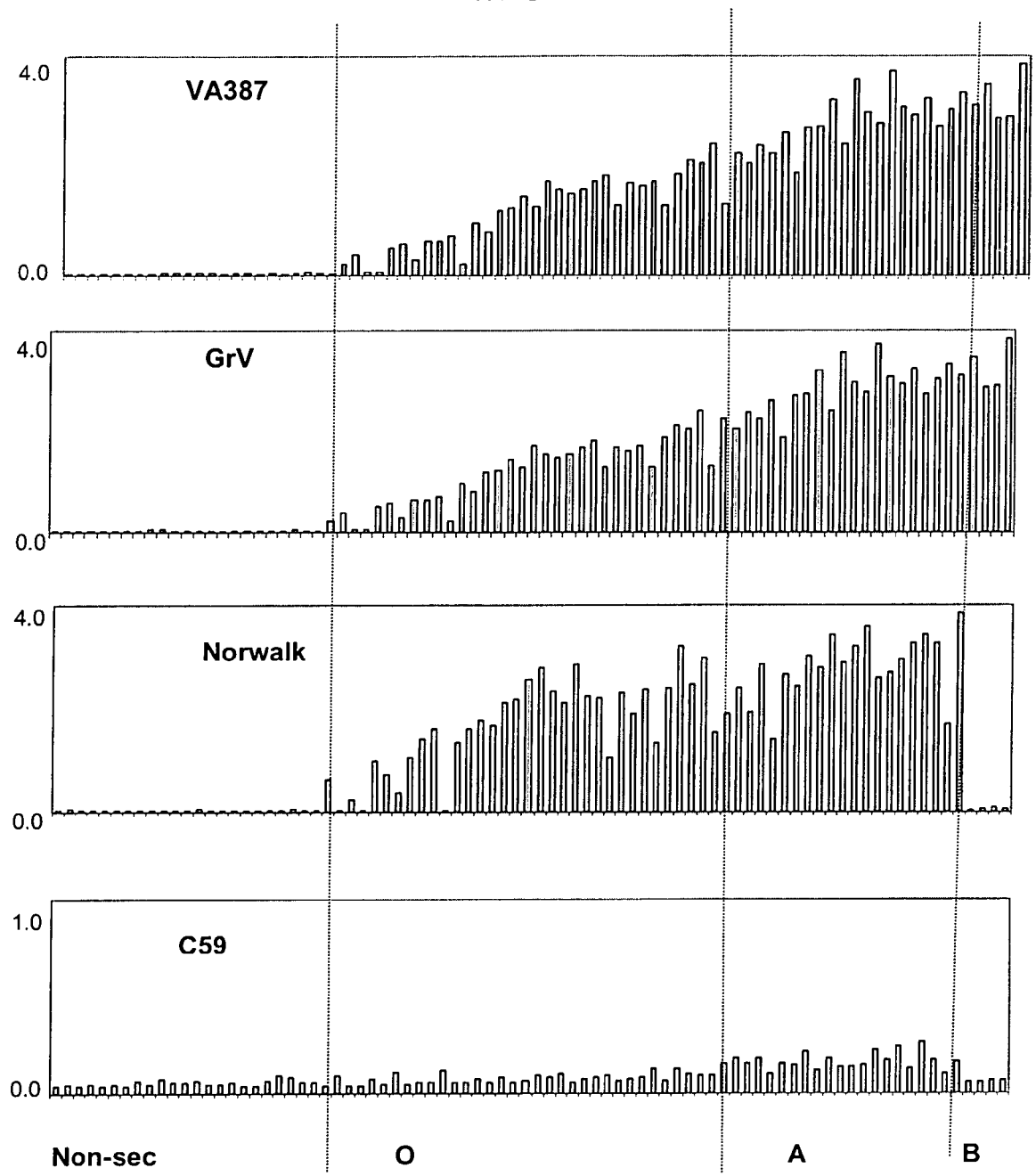
FIGS. 1A-1D show graphic results of the binding of recombinant VLPs of fourteen noroviruses to saliva samples from individuals with different HBGA types, based on the histo-blood phenotypes for secretors (A, B and O blood types) and non-secretors ($Le^-$ and $Le^+$).

Definitions:

As used herein, the terms "Binding Pattern," "BP" or "Binding Patterns" refers to one of the seven specific Binding Patterns provided by this invention. More specifically, "Binding Pattern(s)" refers to the seven Binding Patterns listed below as Binding Pattern #'s 1 through 7, followed by their respective binding characteristics by specific norovirus strains:

1. Binding Pattern #1: norovirus strains that bind A or B, and H epitopes: e.g. norovirus strains VA387 and GrV
2. Binding Pattern #2: norovirus strains that bind A and H epitopes: e.g. norovirus strains Norwalk and C59
3. Binding Pattern #3: norovirus strains that bind A or B epitopes only: e.g. norovirus strains PiV, MxV, HV and MOH
4. Binding Pattern #4: norovirus strains that bind A epitope only (based on the saliva binding assays): e.g. norovirus strain BUDS
5. Binding Pattern #5: norovirus strains that bind non-secretors (Lewis epitope) with strong affinity to H epitope: e.g. norovirus strain Boxer
6. Binding Pattern #6: norovirus strains that bind non-secretors (Lewis epitope) with weak affinity to H epitope: e.g. norovirus strain VA207
7. Binding Pattern #7: norovirus strains that bind only non-secretors (Lewis epitope): e.g. norovirus strain OIF As used herein, the term "biological sample" means one that is obtained from the body fluids or cells of an organism. Examples of an organism include any mammal, and in particular humans, mice, rats, rabbits, goats, guinea pigs, and donkeys. Examples of body fluids include but are not limited to blood, plasma, serum, mucosal fluids, and secreted body fluids such as saliva.

As used herein, the term "blood antigen" refers to a blood antigen selected from a natural human histo-blood group antigen, a synthetic human histo-blood group antigen, and a functionally equivalent molecule that binds to a norovirus with the binding specificity of a human histo-blood group antigen. The functionally equivalent molecule can be an anti-norovirus antibody that binds to a determinant binding site of the norovirus. The blood antigen is typically selected from the group consisting of H antigen, A antigen, B antigen, $Le^a$ antigen, $Le^b$ antigen, and mixtures thereof. The natural blood antigen can be obtained from the biological fluids (saliva, blood, etc.) of individuals of that histo-blood group type. For example, $Le^a$ antigen can be obtained from the body fluid (such as saliva) of a person who is a Lewis positive non-secretor. An antigen can be obtained from a person who is a secretor and of type "A" blood; and so forth. A synthetic antigen is a compound selected from a protein, peptide, oligosaccharide, natural compound, and mixtures thereof, that comprises the analog of the antigenic determinant epitope of the natural blood antigen, which can bind to the determinant binding site of a norovirus with the binding specificity of the antigenic determinant epitope of the natural human histo-blood group antigen. An example of a synthetic antigen can comprise an oligosaccharide conjugated to BSA, and can include, but is not limited to, A trisaccharide-BSA (GalNAc- α1→3 (Fuc-α1→2) Gal β-O-space) NBSA), B trisaccharide-BSA (Gal-α1→3 (Fuc-α1→2) Gal β-O-space) nBSA), Lacto-N-fucopentaose II-BSA [or, Lewis$^a$ trisaccharide], Lacto-N-fucopentaose I-BSA [or H type 1 trisaccharide], and Lacto-N-difucohexaose I-BSA [or, Lewis$^b$ trisaccharide], available from Glycorex AB, Lund, Sweden, and from V-Labs, Inc., Covington, La. The binding specificity of synthetic histo-blood antigens (for example, an oligosaccharide conjugated to BSA) with a norovirus has been demonstrated wherein a specific synthetic histo-blood antigen (for example, A trisaccharide-BSA) loses binding with a norovirus (such as a NV) after digestion to remove the antigenic determinant sugar epitope from the synthetic oligosaccharide with a glycosidase (for example, an α-N-acetylgalactosaminidase for the A trisaccharide-BSA). Thus, the corresponding norovirus could not be bound.

As used herein, the term "competitive inhibition" refers to a mechanism of reversible inhibition of a binding site on a molecule or enzyme where the inhibitor (e.g. a standard compound) resembles the substrate (e.g. an HBGA) and binds to the same point on the molecule (e.g. a norovirus) that the substrate would. Competitive inhibitors do not completely block the molecule from binding to its substrate, and if the concentration of the inhibitor is lowered the binding activity returns to its normal level. In the presence of inhibitor the binding of the substrate to the molecule can still proceed but at a much lower rate, depending on the amount of inhibitor and substrate present.

As used herein, the term "functionally equivalent molecule" means one that can adequately substitute for a compound it is meant to mimic by supplying a function equivalent to the function of the compound. The function that is supplied can include, but is not limited to, the binding specificity of a binding site, an epitope, an active site, a catalytic site, or a recognition site or any combination thereof. A functionally equivalent molecule can substitute for more that one compound, thus combining or providing multiple functions. A functionally equivalent molecule can be a synthetic analog or a naturally occurring compound or portion of a compound. For example, a specific functional domain of a naturally occurring compound can be enzymatically cleaved from the native compound and purified for use. Alternatively, such a domain can be expressed as a recombinant protein in a suitable host and purified for use.

As used herein, the term "incubation" means an interval of time for which an experimental procedure or reaction is allowed to occur. An incubation interval may also be defined as a specified interval of time and a specified temperature at which a biological reaction may be expected to occur.

As used herein, the term "infect" refers to the process by which a virus, such as a norovirus, releases its genome into a cell. In most cases, the process of "infection" causes the cell to replicate the viral genome and produce multiple daughter copies of the parental "infecting" virus.

As used herein, the term "optimiz(e, -ing, -ation)" refers to the empirical experimental process of determining the best conditions at which a biological reaction or series of reactions will occur. Components of the optimization process can include but are not limited to determining the most advantageous incubation time, temperature, chemical constituents, exposure to light, pH, concentrations of the chemical and biological constituents, and especially combinations of these components, in order to achieve an experimental outcome.

As used herein the terms "norovirus," "Norwalk-Like Virus," or "NLV" can be used interchangeably to mean any virus of the norovirus family, and includes, without limitation, the following: Norwalk virus, MOH, Mexico virus (MxV), VA207, VA387, C59, VA115, 02-1419, Hawaii virus (HV), Snow Mountain, Hillington, Toronto, Leeds, Amsterdam, Idaho Falls, Lordsdale, Grimsby, Southampton, Desert Shield virus (DSV), Birmingham, White Rivercap, Parris Island (PiV), Boxer, BUDS, Grimsby virus (GrV), and Operation Iraqi Freedom (OIF).

Each human blood antigen, for example a human histo-blood group antigen (HBGA), can bind to the virus-like particle (VLP) of one, and usually to at least 2, norovirus strains. Conversely, each norovirus will bind to at least one, and usually with 2 or more human blood antigens. The blood antigen binds to the norovirus at the blood antigen's antigenic-determinant epitope (the sugar moiety). The norovirus binds to the blood antigen at the determinant binding site on the VLP's protein structure. The group of blood antigens to which a norovirus will bind is referred to as that norovirus strain's antigen binding pattern.

For example, previously five norovirus strains (strains VA387, MOH, NV, 02-1419, and VA207) have been shown to provide a specific pattern of binding with one or several of the five blood antigens: the H antigen, the A antigen, the B antigen, the Le$^a$ antigen and the Le$^b$ antigen. The VA387 strain binds to the A, B, H and Le$^b$ blood antigens, but does not bind to Le$^a$ antigen. The prototype NV strain binds to A, H and Le$^b$ antigens, but does not bind to B or Le$^a$ antigens. Strain 02-1419 binds to A antigen, but does not bind to H, B, Le$^b$, or Le$^a$ antigens. MOH strain binds to A and B antigens, but does not bind to H, Le$^b$, or Le$^a$ antigens. The VA207 strain binds to Le$^a$ antigen, but does not bind to H, A, B or Le$^b$ antigens. Conversely, histo-blood group antigen A is bound by the 387, NV, 02-1419, and MOH strains, but not bound by the 207 strain. The blood antigen B is bound by the 387 and MOH strains, but not bound by the NV, 02-1419, and VA207 strains. The blood antigen H and the Le$^b$ antigens are bound by the VA387 and NV strains, but not bound by the MOH, 02-1419, and VA207 strains. The blood antigen Le$^a$ is bound by the VA207 strain, but not bound by the VA387, NV, 02-1419, and MOH strains. These binding patterns are summarized in Table A.

TABLE A

Binding of norovirus strains to Human Histo-blood group Antigens

| Norovirus | Human Histo-Blood Antigen | | | | |
|---|---|---|---|---|---|
| | A | B | H | Le$^b$ | Le$^a$ |
| 387 | B | B | B | B | — |
| NV | B | — | B | B | — |
| MOH | B | B | — | — | — |
| 207 | — | — | — | — | B |
| 02-1419 | B | — | — | — | — |

B = Binding
— = minimal or no binding

Other noroviruses among the dozens of known strains can also bind to at least one histo-blood group antigen. Many of these other norovirus strains have a similar binding pattern to those above based on the specificity of their determinant binding site for the antigenic determinant epitopes of the blood antigens, and are described in more detail below. From the binding patterns of these other norovirus strains, similar binding tables can be prepared that show a unique binding pattern with the blood antigens in the respective ABH and Lewis blood groups.

Without being bound by any particular theory, each known norovirus has at least one determinant binding site that can be bound by the determinant epitope of at least one of the histo-blood group antigens of the ABH, and Lewis blood groups. Infection of a host by a norovirus occurs when a norovirus is recognized and bound by a histo-blood group antigen of the host's phenotype. The association of the host's blood antigen with receptors on the epithelial cells of the host brings the norovirus into proximity with the epithelial cell. It is believed that this proximity of the norovirus to an epithelial cell renders the cell susceptible to infection when the norovirus releases its genetic material into the cell. Disruption of the binding between the norovirus and the host's blood antigen(s) eliminates the opportunity for the norovirus to come into close proximity with the epithelial cells, and diminishes their susceptibility to infection.

It has been shown that some individuals do not become infected when exposed to certain strains of norovirus strains. In most of these cases, the host does not have a blood antigen that could bind with the particular norovirus. Without a host blood antigen to deliver the norovirus into proximity with the host's epithelial cells, no infection could occur.

The present invention includes novel compositions, methods and kits for use in detecting a norovirus in a biological sample, for detecting histo-blood group antigens in a biological sample, and for a method of screening for a compound that can inhibit binding between a norovirus and a human histo-blood group antigen.

Detecting a Norovirus in a Biological Sample

The present invention can include a method to detect if a person has a norovirus infection. The method can also be used to identify the specific norovirus that has infected the person, or to identify that a virus belonging to one of a group of norovirus strains has infected the person. A person infected with a norovirus will generally pass the norovirus through the gastrointestinal (GI) tract with the stool, whereby stool sample collected from the infected person will contain the virus. Ordinarily, only a single type of norovirus will have infected a person at one time.

The biological sample suspected of containing a norovirus, typically a stool sample, is contacted with at least one, and typically more than one, blood antigen as a target. Further, the method typically uses at least 2 and more typically all of the blood antigens. The plurality of blood antigens is typically contacted separately to allow the norovirus in the biological sample to contact each blood antigen individually. However, a mixture of two or more blood antigens can be placed together into a single area depending on the method of detection and the specificity of detection required.

A complex can form between the norovirus and the blood antigen provided that the norovirus and the blood antigen have a binding affinity for each other, and that the contacting step provides sufficient incubation time and conditions to form the norovirus-blood antigen complex.

The resulting norovirus-blood antigen complex is then detected. After the biological sample has been contacted and complexed, the non-binding material of the biological sample is washed from the complex and/or target. The non-binding material includes any norovirus that does not bind to the blood antigen target. Detection and identification monoclonal antibodies (MAbs) or polyclonal antibodies can be used for detecting the norovirus-blood antigen complex.

The detection can be either a direct detection method or an indirect detection method, or both. The direct detection of a norovirus bound to a blood antigen can be made by contacting the norovirus-blood antigen complex with a detectable norovirus antibody that has a norovirus binding site that binds to a non-determinant norovirus epitope (i.e., an epitope other than the determinant binding site) of the norovirus. After optimized contacting between the complex and the detectable norovirus antibody, any unbound norovirus antibody is washed away. The norovirus antibody is then detected, which determines that a norovirus has bound to the blood antigen target. The norovirus antibodies can be used one by one to detect whether a specific norovirus is present in the complex, or can be used as a group (cocktail) of antibodies to detect whether any one of the group of norovirus strains is present in the complex.

Detectable norovirus antibodies that bind to a non-determinant norovirus epitope of a norovirus include rabbit and guinea pig antibodies against a particular norovirus strain, for example Norwalk Virus, strain 387, strain 207, strain MOH, Mexico strain, strain 02-1419, and any other norovirus strain, respectively.

The indirect detection of a norovirus bound to a blood antigen can be made by contacting the blood antigen target with a detectable anti-antigen antibody having an anti-antigen binding site that binds specifically to the antigen-determinant epitope of the blood antigen. After optimized contacting between the target antigen and the detectable anti-antigen antibody, any un-bound anti-antigen antibody is washed away from the blood antigen target. The anti-antigen antibody is then detected, which determines that the anti-antigen antibody has bound to the blood antigen target. If the anti-antigen antibody can not be detected, then one can presume that a norovirus has bound to that blood antigen target, and has blocked binding by the anti-antigen antibody by competitive inhibition. If the detectable anti-antigen antibody can bind to the blood antigen target and is detected, then it can be concluded that a norovirus had not bound to antigenic determinant epitope of that blood antigen target.

Detectable anti-antigen antibodies that bind specifically to the antigen-determinant epitope of blood antigen(s) include MAbs BG-4 anti-H type 1, BG-5 anti-Le$^a$, BG-6 anti-Le$^b$, BG-7 anti-Le$^x$, and BG-8 anti-Le$^y$, available from Signet Laboratories, Inc. (Dedham, Mass.), MAbs BCR9031 anti-H type 2, BCR 9010 anti-A, and BCRM 11007 anti-B, available from Accurate Chemical & Scientific Corporation (Westbury, N.Y.), 7-LE anti-Le$^a$, 2-25LE anti-Le$^b$, 19-OLE anti-H type 2, and 3-3A anti-A, available from Dr. J. Baca (Villejuif, FR), and ED3 anti-B available from Dr. A. Martin (Rennes, FR).

Detectable anti-norovirus antibodies that binding specifically to norovirus strains include rabbit and guinea pig hyperimmune antibodies against individual strains of norovirus strains, and hyperimmune antibodies against a pooled antigens that include, but are not limit to, the NV, VA387, VA207, 02-1419, and MOH. Pooled hyperimmune antibodies are available as Lot # Rabbit 15, Rabbit 16, and Rabbit 17 from Xi Jiang, Children's Hospital Research Center, Cincinnati, Ohio.

The blood antigen can be arranged as targets in discrete areas to determine the binding pattern for the norovirus, which can also serve as a confirmation of the identity of the norovirus, or class of norovirus, since each norovirus has a unique binding pattern with the blood antigens.

The invention can also embody a kit for detecting a norovirus in a biological sample, comprising: a) a container for holding a biological sample (usually a stool sample from a human that is suspected of containing a norovirus), the container comprising a media having thereon affixed at least one blood antigen capable of complexing with a norovirus; and b) an assay for the detection of a complex of the norovirus blood antigen.

The assay can comprise an ELISA that comprises a detectable norovirus antibody that has a norovirus binding site that binds to a determinant or non-determinant epitope of the norovirus of the Norovirus-blood antigen complex. Since the identity of a norovirus in a biological stool sample is usually unknown, a plurality of the detectable norovirus antibodies is typically used. The assay also optionally includes a means for washing away any unbound biological sample and unbound norovirus VLPs, and for washing away any unbound detectable norovirus antibody from the media. The assay can also comprise an ELISA that comprises an anti-antigen antibody that binds to the antigen-determinant epitope of the blood antigen.

Detecting a Histo-Blood Group Antigen in a Biological Sample

The present invention can comprise a method to determine the susceptibility of an individual to infection by a particular norovirus strain. This method detects for and determines the particular type of histo-blood group antigens (HBGAs) present in a biological sample.

The biological sample is typically a saliva sample, which can be obtained in numerous ways known in the art, but the sample can also be blood, vascular endothelial cells, intestinal epithelial cells, cervical epithelial cells, urothelial epithelial cells, pulmonary epithelial cells, mammary epithelial cells, breast milk, urine, or feces. Typically the saliva sample is treated by boiling to inactivate native antibodies which may interfere with the assays. The treated sample is centrifuged to remove any debris. The supernatant of the sample, containing HBGAs, is then collected and stored frozen before use in the test. The biological sample is then contacted with at least one norovirus strain as a target, and incubated to form a complex between a HBGA present in the saliva and the norovirus. Typically at least two norovirus strains are used, and are contacted separately by the saliva sample. The norovirus is typically one that has a known binding pattern for the HBGAs.

The resulting HBGA-norovirus complex is then detected. After the biological sample has been contacted and complexed, the non-binding material of the biological sample is washed from norovirus target. The non-binding material includes any HBGA from the sample that does not bind to the norovirus target. Detection and identification hyperimmune or monoclonal antibodies can be used for detecting the HBGA-norovirus complex.

The typical detection steps comprise contacting the norovirus targets with a standard compound, typically an anti-norovirus antibody that binds at a determinant binding site of the respective norovirus. After washing away any unbound anti-norovirus antibody, any remaining anti-norovirus antibody bound to a norovirus target is detected. Binding of the anti-norovirus antibody to the norovirus target indicates that the norovirus had not bound to any HBGAs in the sample.

Conversely, the absence of binding by the anti-norovirus antibody to the norovirus target can be presumed to indicate that a HBGA had already complexed with the norovirus target. In one embodiment, the method comprises contacting a saliva sample with separate targets of various norovirus strains, including strains VA387, MOH, NV, 02-1419, VA207, GrV, Boxer, OIF, C59, PiV, HV, MxV, DSV, BUDS, VA115, and mixtures thereof. The binding patterns of the anti-norovirus antibodies to the norovirus targets indicate the HBGA-norovirus binding pattern for the biological sample, and thus the type of HBGAs present in the biological sample. Thus, an individual with these HBGAs will be susceptible to the norovirus strains tested.

Other norovirus strains are shown below to have specific binding patterns with blood antigens according to the present invention. In an alternative embodiment, the method comprises contacting a known norovirus with a biological sample target having a blood antigen such as a HBGA. Detection of the norovirus-blood antigen complex can be detected by contacting the biological sample target with a detectable norovirus antibody that binds to a determinant or non-determinant epitope of the respective norovirus. The pattern of binding of each known norovirus to the blood antigen can reveal the type of blood antigen present in the biological sample.

The presence of a norovirus, and its HBGA specificity or binding pattern, can be determined by sampling a food or water suspected of being contaminated with a norovirus, or by a biological sampling (usually, a stool sample) of a person suffering from symptoms of a norovirus infection (such as vomiting and diarrhea), and assaying the food, water, or biological sample for the presence of a norovirus. The method provides a means for detecting a norovirus in a biological, water, and/or food sample suspected of containing a norovirus, by contacting the biological sample with human histo-blood group antigens targets, or a functionally equivalent molecule thereof, and then detecting the Norovirus-blood antigen complex.

Antibody detection means: Detectable anti-antigen antibodies that bind specifically to the antigenic determinant epitope of blood antigen(s) (e.g. HBGAs) include: for an H antigen, BG-4; for an A antigen, BCR 9010; for a B antigen, BCRM 11007; for a $Le^a$ antigen, BG-5; and for a $Le^b$ antigen, BG-6. These are available from Signet Laboratories, Inc. (Dedham, Mass.) and Accurate Chemical & Scientific Corporation (Westbury, N.Y.).

Detectable anti-norovirus antibodies, detectable norovirus antibodies, detectable anti-antigen antibodies and detectable antigen antibodies can be detected, or made detectable, in several ways that are well known to one of ordinary skill in this art. For detection purposes, an antibody or antigen is, in general, linked to a molecule that emits a signal or catalyzes an enzymatic change in a substrate. In either case, a colorimetric read-out is obtained. In the case of catalysis of a substrate, the color change may be visible to the naked eye, and thus may be conveniently used when performing a few tests, typically less than 10-12. When an array of test samples are measured, the typical spectrophotometric method is a microtiter plate reader, of which there are many commercially available models.

Another detectable antibody can comprise an antibody or antigen linked to a photochrome molecule that can be detected when viewed with an appropriate light wavelength and filter. For example, fluorescein isothyocyanate, phycoerythrin, Texas Red, or other fluorescent moieties may be covalently linked to antibody or antigen and detected spectrophotometrically. Another useful means of making a detectable antibody involves linking a catalyst horse-radish peroxidase (HRP) to an antibody or antigen to be detected, and visualizing by addition of a substrate solution. The resultant color change can be measured spectrophotometrically. A biotin-conjugated antibody is another useful detectable antibody form, which following incubation with streptavidin-fluorescein can be measured spectrophotometrically. A biotin-avidin complex can also be detected using commercially available kits. The biotin is linked to the antibody, then complexed with avidin linked to an enzyme that may be detected by staining. Vectastain™ ABC kit is an example of this staining technique.

Inhibiting the Binding Activity of a Norovirus Toward a Blood Antigen

The present invention includes a method of identifying a first test compound that inhibits the binding activity of a known norovirus strain with a blood antigen. The method comprises the steps of:

a) contacting the known norovirus target with a first test compound;

b) contacting the known norovirus target with a first standard compound that is known to bind with a determinant binding site of the norovirus;

c) determining whether the binding of the first standard compound is decreased in the presence of the test compound, the decrease in binding being an indication that the first test compound inhibits the binding activity of the norovirus toward the first standard compound.

The first standard compound that is known to bind with the determinant binding site of the norovirus can be a native histo-blood antigen, selected from the group consisting of the ABH blood group antigens, the Lewis blood group antigens, and mixtures thereof. The ABH blood group antigens can be selected from H antigen, A antigen, B antigen and a mixture thereof, while the Lewis group antigens can be either the $Le^a$ (non-secretor) antigen or the $Le^b$ (secretor) antigen. The first standard compound can also comprise a synthetic oligosaccharide with one or more conjugated moieties having receptor binding properties that are functionally equivalent to those of the antigenic determinant epitopes of human histo-blood group antigens. Such compounds are known to have specific binding to human histo-blood antigens, and are commonly used for determining human blood type. Examples of such first standard compounds include A trisaccharide-BSA (GalNAc-α1→3 (Fuc-α1→2) Gal β-O-space) nBSA), B trisaccharide-BSA (Gal-α1→3 (Fuc-α1→2) Gal β-O-space) NBSA), Lacto-N-fucopentaose II-BSA [or, $Lewis^a$ trisaccharide], Lacto-N-fucopentaose I-BSA [or H type 1 trisaccharide], and Lacto-N-difucohexaose I-BSA [or, $Lewis^b$ trisaccharide], available from Glycorex AB, Lund, Sweden, and from V-Labs, Inc., Covington, La.

The step of determining whether the binding of the first standard compound is decreased comprises the step of detecting the presence of the standard compound on the norovirus target. The first standard compound can comprise a detectable linked molecule that can emit a signal or catalyze an enzymatic change in a substrate. The first standard compound can also be detected by contacting the norovirus target with a detection compound, such as a detectable antibody, which selectively binds to the standard compound, and then detecting the antibody.

A control test is also conducted to detect the binding of the first standard compound with the norovirus target without pre-contacting of the first test compound. The detection value for the test leg is then compared with the detection value for the control leg to determine whether the binding of the first standard compound had decreased in the presence of the first test compound.

The first test compound is typically selected from the group consisting of a protein, a polypeptide, an oligosaccharide, another histo-blood group antigen, a natural or synthetic compound, and a poly- and monoclonal antibody. An oligosaccharide is a typical compound, since it is generally regarded as safe. A monoclonal antibody to the determinant binding site of the norovirus can be prepared, and isolated by procedures that are well known to those skilled in the art. The first test compound can also be a molecularly-engineered compound that is designed to have a binding site geometry that is complimentary to the determinant binding site of the norovirus.

A first compound that can competitively bind with a norovirus and thereby prevent a blood antigen from binding can also be selected based on a mimicking of the chemical structure, geometry, or binding specificity of the antigenic-determinant epitope of a human histo-blood antigen that is known to bind with the determinant binding site of the particular norovirus.

A first test compound of the present invention can be selected from compounds that have the same, or substantially the same, chemical structure as the human histo-blood group antigen's antigenic determinant epitope. The antigenic determinant epitope of the H antigen comprises the Fuc-α1→2 structure. The antigenic determinant epitope of the A antigen comprises the GalNAc-α1→3 structure. The antigenic determinant epitope of the B antigen comprises the Gal-α1→3 structure. The antigenic determinant epitope of the $Le^a$ antigen comprises the Fuc-α1→3/4 structure(s). The antigenic determinant epitope of the $Le^b$ antigen comprises the Fuc-α1→2 structure. A typical compound is a synthetic or natural oligosaccharide that comprises one or more moieties selected from the structures Fuc-α1→2, GalNAc-α1→3, Gal-α1→3, Fuc-α1→3/4, and mixtures thereof.

Typically the compounds is a carbohydrate selected from the group consisting of fucosyl α1→3/4 N-acetyl glycosyl globoside (F3AG), a stabilized, synthetic F3AG analogue, and mixtures thereof, in an amount that inhibits binding of norovirus strain 207 to gastroepithelium of a non-secretor individual; a carbohydrate selected from the group consisting of fucosyl α1→2 galactose globoside (F2G), a stabilized, synthetic F2G analogue, and mixtures thereof, in an amount that inhibits binding of norovirus strain 387 to gastroepithelium of a secretor individual; a carbohydrate selected from the group consisting of N-acetyl galactosyl α1→3 galactosyl globoside (AG3G), N-acetyl galactosyl α1→4 galactosyl globoside (AG4G), a stabilized, synthetic AG3G analogue, a stabilized, synthetic AG4G analogue, and mixtures thereof, in an amount that inhibits binding of norovirus strain MOH to gastroepithelium of a secretor individual; and a carbohydrate selected from the group consisting of galactosyl α1→3 galactosyl globoside (G3G), galactosyl α1→4 galactosyl globoside (G4G), a stabilized, synthetic G3G analogue, a stabilized, synthetic G4G analogue, and mixtures thereof, in an amount that inhibits binding of norovirus strain MOH to gastroepithelium of a secretor individual.

A first test compound can also be selected from compounds that have the same geometric structure as the human histo-blood group antigen's antigenic determinant epitope. The nucleotide and amino acid sequences of the norovirus capsid genes of several norovirus strains, and the three-dimensional structure of the prototype NV, are known, and could be used to model ligand-receptor (binding site-epitope) interaction for the engineering of such compounds.

A first test compound can also be selected from a compound that has the binding specificity of the antigenic determinant epitope of a blood antigen, and functionally equivalent molecules thereof. Such compounds can include monoclonal antibodies. A typical antibody is an anti-antibody to the antigenic determinant epitope. An example of such an antibody is the 9C3 Mab that can bind at the determinant binding site of the NV with the binding specificity of the antigenic determinant epitope of the H-type blood antigen, and is available from Dr. Xi Jiang, Children's Hospital Research Center, Cincinnati, Ohio.

Inhibiting the Binding Activity of a Blood Antigen Toward a Norovirus

The invention includes a method of identifying a second test compound that inhibits the binding activity of a blood antigen with a norovirus. The method comprises the steps of:

a) contacting a histo-blood group antigen target with a second test compound;

b) contacting the blood antigen with a second standard compound that is known to bind with an antigenic determinant epitope of the blood antigen; and c) determining whether the binding of the second standard compound is decreased in the presence of the second test compound, the decrease in binding being an indication that the second test compound inhibits the binding activity of the blood antigen toward the second standard compound.

The second standard compound that is known to bind with the antigenic determinant epitope of the blood antigen can be a recombinant norovirus that retains the VLP shape and structure of the wild-type norovirus, but has been rendered reproductively inert by molecular engineering methods known to those skilled in the art.

The step of determining whether the second binding of the standard compound is decreased comprises the step of detecting the presence of the second standard compound on the blood antigen target. The second standard compound can comprise a detectable linked molecule that can emit a signal or catalyze an enzymatic change in a substrate. The second standard compound can also be detected by contacting the blood antigen target with a detection compound, such as a detectable antibody, which selectively binds to the second standard compound, and then detecting the antibody.

A control test is also conducted to detect the binding of the second standard compound with the blood antigen target without pre-contacting of the second test compound. The detection value for the test leg is then compared with the detection value for the control leg to determine whether the binding of the second standard compound had decreased in the presence of the second test compound.

The second test compound is typically selected from the group consisting of a protein, an oligosaccharide, another histo-blood group antigen, a natural compound, and a monoclonal antibody. An oligosaccharide is a typical compound, since it is generally regarded as safe. A monoclonal antibody to the antigenic determinant epitope of the blood antigen can be prepared, and isolated by procedures that are well known to those skilled in the art. The second test compound can also be a molecularly-engineered compound that is designed to have a binding site geometry that is complimentary to the antigenic determinant epitope of the blood antigen.

The invention also includes a hybridoma that can produce a monoclonal antibody as a second test compound, made constructed by a means well known in the art.

A second test compound that can competitively bind with a blood antigen and thereby prevent a norovirus from binding can also be selected based on a mimicking of the chemical structure, geometry, or binding specificity of the determinant binding site of a norovirus that is known to bind with the antigenic determinant epitope of the particular blood antigen.

A second test compound of the present invention can be selected from compounds that have the same, or substantially the same, chemical structure and/or geometric structure as the norovirus strain's determinant binding site. The nucleotide and amino acid sequences of the norovirus capsid genes of several norovirus strains, and the three-dimensional structure of the prototype NV, are known, and could be used to model ligand-receptor (binding site-epitope) interaction for the engineering of such compounds.

A second test compound can also be selected from compounds that have the binding specificity of the norovirus strain's determinant binding site.

Other Embodiments of the Invention

The invention also includes a medicament and a pharmaceutical composition comprising an active compound selected from the group consisting of a first test compound, a second test compound, and a mixture thereof; and a pharmaceutically acceptable diluent, carrier or excipient. A typical composition comprises at least one, and typically two or more, first test compounds that can prevent the host blood antigen from binding with any norovirus in vivo, thereby inhibiting an infection, or treating an infection, of the host by the norovirus. Typically, the first test compounds prevent any host blood antigen selected from the ABO blood type antigens, and the Lewis blood antigens, from binding with any norovirus in vivo.

Non-limiting examples of suitable pharmaceutically acceptable carriers include phosphate buffered saline solutions, water, emulsions including oil/water emulsions, various types of wetting agents such as detergents, and sterile solutions. Compositions comprising such carriers can be formulated by well known conventional methods. Compositions can also comprise liquid or viscous compositions that can coat and/or line the surface of the GI tract, thereby placing the active compounds in direct proximity with the epithelial cells.

The invention also relates to a method for preventing an infection of a host by a norovirus, by administering to the host an effective preventative amount of a prevention compound that inhibits binding of the norovirus in vivo to a histo blood group antigen of the host. The invention can also relate to a method for treating an active infection of a host by a norovirus, by administering to the host an effective treatment amount of a treatment compound that inhibits binding of the infecting norovirus in vivo to a histo blood group antigen of the host.

The invention further relates to a use of a preventative compound in a medicament or pharmaceutical for the prevention and treatment in a mammal of an infection by a norovirus, wherein the preventative compound has the binding specificity of the antigenic determinant of a human histo-blood group antigen.

The prevention compound can be selected from the first test compound, the second test compound, or a mixture thereof. The treatment compound can be selected from the first test compound, the second test compound, or a mixture thereof.

Typical are medicaments and pharmaceutical compositions comprising at least one of, though typically a plurality of, a prevention or treatment compound, which can bind with any infecting strain of norovirus. When an outbreak of a norovirus occurs, the time to isolate and detect the specific strain of norovirus for pinpoint treatment can delay administration of treatment or prevention compositions to a population of infected or susceptible persons. Typically, a combination of treatment or prevention compounds in a single medicament or pharmaceutical that can singularly or jointly bind with any strain of norovirus, will ensure effective treatment or prevention of infection, regardless of the particular strain(s) of virus involved.

The effective prevention amount of the prevention compound is an amount sufficient to bind any norovirus that is present in the gastrointestinal system of a host who had consumed a food or water source contaminated by the norovirus. Ordinarily, these amounts of norovirus would be very low. For this reason, a typical prevention compound is a first test compound that binds with the norovirus to prevent its further binding with the host blood antigens. The amount of the prevention compound to be consumed will typically range from about 100 to about 10,000 units per dose, more typically from about 1,000 to about 10,000 units per dose, where a unit defines the amount of the compound to bind with a single virus particle. Typically, according to the method of the invention, a dose of the medicament comprising the compound would be consumed by the host just prior to, while, or just after, consuming a food or water suspected of being contaminated with a norovirus.

The effective treatment amount of the treatment compound is an amount sufficient to bind any norovirus that are progeny from those infected within the epithelial cells of the gastrointestinal system of a host. Ordinarily, these amounts of norovirus would be high compared to amounts of norovirus strains found in a contaminated water or food. The amount of the treatment compound to be consumed will typically range from about 1,000 to about 100,000 units per dose, more typically from about 10,000 to about 100,000 units per dose, where a unit defines the amount of the compound to bind with a single virus particle. Typically, according to the method of the invention, a dose of the medicament comprising the compound would be consumed by the host periodically until the symptoms of the infection have dissipated and stopped. Since any consumed treatment compound would pass through the gastrointestinal system in the ordinary course, the periodic dosage is typically about every 1 to 4 hours.

In the present application, binding and blocking experiments were performed using saliva, synthetic oligosaccharides and monoclonal antibodies (MAbs) to characterize norovirus binding specificities. The results showed that noroviruses are highly diverse in recognizing human HBGAs, and seven Binding Patterns are described based on the fourteen strains studied. By further analyzing the Binding Patterns based on three major antigenic epitopes of HBGAs, seven Binding Patterns have been grouped into two major binding groups (the A/B, H-binding group and the Lewis-binding group), and a model of the norovirus/HBGA interaction is proposed. Strains in the A/B, H-binding group recognize the A and/or B and H antigens, but not the Lewis antigens, while strains in the Lewis-binding group react only to the Lewis and/or H antigens. The seven Binding Patterns are represented by fourteen strains: VA387, GrV, Norwalk Virus, C59, MxV, MOH, VA207, VA115, PiV, BUDS, Boxer, OIF, DSV, and HV, representing 13 genetic clusters of noroviruses.

This classification resulted in a model of the norovirus/HBGA interaction. Each histo-blood group antigen (HBGA) can bind to the norovirus virus-like particle (VLP) of one, and typically at least two, noroviruses. Conversely, each norovirus will bind to at least one, and typically with two or more HBGAs. The HBGA binds to the norovirus at the blood antigen's antigenic-determinant epitope (the sugar moiety). The norovirus binds to the blood antigen at the determinant binding site on the VLP's protein structure. The group of blood antigens to which a norovirus will bind is referred to as that norovirus' antigen binding pattern.

Phylogenetic analyses showed that strains with identical or closely related binding patterns tended to be clustered. However, strains in both binding groups can be found in both genogroup I and II, suggesting that noroviruses have a wide spectrum of host range, and that human HBGAs play an important role in norovirus evolution.

To ensure the specificity of synthetic oligosaccharides used in the assays, validation experiments using known HBGA-specific MAbs were also performed. Finally, to determine the potential interaction of different epitopes of HBGAs in norovirus binding, cross-blocking experiments using saliva and oligosaccharides as the blocking agents were performed. Following a brief discussion of the materials and methods for these experiments, the results of the binding and blocking experiments are disclosed below.

Virus-Like Particles (VLPs) of Noroviruses

VLPs of fourteen strains representing thirteen genetic clusters of norovirus produced from baculovirus were used, including genogroup 1: Boxer (AF538679), C59 (AF435807), Norwalk virus (M87661), Desert Shield virus (DSV; U044469), VA115 (AY038598); and genogroup II: BUDS (AY660568), Grimsby (GrV; AJ004864), Hawaii (HV; U07611), Mexico (MxV; U22498), MOH (AF397156), Parris Island (PiV; AY652979), VA387 (AY038600), VA207 (AY038599), and Operation Iraqi Freedom 031998 (OIF, AY675554).

The procedures of production of norovirus VLPs in insect cell culture have been previously disclosed in the parent application, which is incorporated herein by reference in its entirety. Briefly, a cDNA from the 3' end of the genome containing the viral capsid gene (ORF2) and a minor structural gene (ORF3) were cloned from the viral RNA extracted from stool specimens. The recombinant baculoviruses carrying the viral capsid genes were constructed from the cloned cDNAs using Bac to Bac expression system, according to the manufacturer's instructions (Invitrogen Life Technologies, Carlsbad, Calif.). Norovirus VLPs were produced in Sf9 or H5 insect cell cultures. VLPs were partially purified by sucrose gradient centrifugation and stored at −70° C. Protein concentrations were determined by measuring $OD_{280}$ and by comparison with a bovine serum albumin standard in SDS-polyacrylamide gel.

Binding of Norovirus VLPs to Saliva Samples

Saliva samples from healthy adult volunteers were collected under an approval of human subject research protocol by the Institutional Review Board at the Cincinnati Children's Hospital Medical Center. Additional saliva samples were collected from US military personnel as part of an outbreak surveillance of acute gastroenteritis under a Department of Defense project (Scott Thornton). The saliva-binding assays were performed as described previously. Briefly, microtiter plates (Dynex Immulon, Dynatech, Franklin, Mass.) were coated with saliva at a dilution of 1:1,000 to 5,000 in phosphate buffer saline (PBS, pH 7.4). To avoid potential norovirus-specific antibodies in the saliva that may interfere in the receptor binding assays, saliva samples were boiled before being used in the assays. After removing the unbound saliva and blocking with 5% dried milk (Blotto), baculovirus-expressed norovirus VLPs at a concentration of 0.4-1.0 μg/mL in PBS were added. The bound VLPs were detected using a pooled guinea pig anti-norovirus antiserum (dilution of 1:3,000), followed by addition of horseradish peroxidase (HRP)-conjugated goat anti-guinea pig IgG (ICN, Aurora, Ohio).

The pooled guinea pig anti-norovirus antiserum was a mixture of hyper-immune sera of 3 groups of guinea pigs cross-immunized with three sets of recombinant norovirus capsid antigens. Set 1 included Norwalk virus, C59 and VA115; set 2 included VA387, Mx, GrV and HV; and set 3 included VA207 and MOH. The pooled guinea pig anti-norovirus antiserum recognized recombined capsid proteins of all 14 norovirus strains studied.

Binding of VLP to Synthetic Oligosaccharides Containing Human HBGA Epitopes

Microtiter plates were coated with synthetic oligosaccharide-BSA conjugates containing human HBGA epitopes at a concentration of 20 μg/mL at 4° C. overnight. Oligosaccharide-PAA-biotin conjugates (2 μg/mL) were coated to microtiter plates by means of streptavidin. After blocking with 5% Blotto, norovirus VLPs were added at 0.4-1.0 pg/mL. The captured VLPs were detected by the same procedures described above.

Oligosaccharides conjugated with two types of carriers were used in this study, including: (1) polyacrylamide (PAA)-biotin conjugates:
(a) H type 3-, type A- and type B-disaccharides;
(b) Le$^a$-, Le$^x$-, H type 1-, H type 2-, type A- and type B-trisaccharides; and
(c) Le$^b$, Le$^y$-, sLe$^a$-, and sLe$^x$-tetrasaccharides (GlycoTech Corporation, Rockville, Md.);
and (2) bovine serum albumin (BSA) conjugates:
(a) A-trisaccharide-BSA {[GalNAc α 1-3 (Fuc α 1-2) Gal β-O-spacer]$_n$-BSA]}} and (b) B-trisaccharide-BSA {[Gal α 1-3 (Fuc α 1-2) Gal β-O-spacer]$_n$-BSA},
both BSA conjugates containing
(i) a 5-atom spacer (Glycorex AB, Lund Sweden),
(ii) a 20-atom spacer (V-Labs, Inc., Covington, La.),
and (iii) a 3-atom spacer (V-Labs, Inc., Covington, La.).

Validation of Synthetic Oligosaccharide Conjugates by Monoclonal Antibodies

To determine the specificity of individual oligosaccharide products, we performed binding assays of the products with monoclonal antibodies (MAbs) specific for HBGAs. Oligosaccharide-BSA conjugates (20 μg/mL) were coated directly while oligosaccharide-PAA-biotin conjugates (2 μg/mL) were coated through streptavidin (10 μg/mL) as anchor. After removal of the uncoated conjugate and blocking with 5% Blotto, MAbs were added at a dilution of 1:100 to 1:200. The captured MAbs were detected using horseradish peroxidase (HRP)-conjugated goat anti-mouse IgG or IgM (ICN, Aurora, Ohio). MAbs used in this study included: MAbs anti-B (BG-3), anti-H type 1 (BG-4), anti-Le$^a$ (BG-5), anti-Le$^b$ (BG-6), anti-Le$^x$ (BG-7) and anti-Le$^y$ (BG-8) (Signet Laboratories, Inc., Dedham, Mass.), MAbs anti-H type 2 (BCR9031), anti-A (BCR9010) and anti-B (BCRM (11007) (Accurate Chemical & Scientific Corporation, Westburg, N.Y.).

Blocking Of Norovirus Binding to Saliva by MAbs

The same conditions of saliva binding assays described above were used. For blocking, saliva-coated plates were pre-incubated with MAbs at a dilution of 1:5 to 1:10 for 1 hour at 37° C. before adding norovirus VLPs to the plate. The levels (%) of blocking were calculated by comparing the OD$_{450}$ values between wells with or without incubation with a MAb.

Cross-Blocking Assays with Synthetic Oligosaccharide Conjugates.

The same conditions of oligosaccharide-binding assays described above were used. For blocking, norovirus VLPs were pre-incubated with 20 μg/mL of BSA-oligosaccharide conjugates or 2 μg/mL of PAA-biotin oligosaccharide conjugates for 1 hour at 37° C. before transferring to the oligosaccharide-coated plate. The levels (%) of blocking were calculated from the OD$_{450}$ values between wells with or without pre-incubation with an oligosaccharide.

Cross-Blocking Assays with Saliva Samples

The same conditions of saliva-binding assays with the principle of the oligosaccharide-blocking assays described above were used except saliva samples were used for both coating and blocking. Saliva samples containing specific HBGAs were selected from our saliva bank and the blood types of the saliva samples were determined by the MAb typing assays.

Sequencing and Phylogenetic Analysis

Sequencing was performed either directly with RT-PCR (reverse transcription-polymerase chain reaction) products or after cloning into pGEM-T vector (Promega, Madison, Wis.). Sequencing reactions were read on an ABI PRIZM 3700 DNA analyzer. Besides the previously mentioned, the following capsid sequences published in the GenBank were used in the phylogenic analysis: Alphatron (AF195847), Amsterdam (AF195848), Arg320 (AF190817), Chiba (AB022679), Hesse (A-F093797), Hillingdon (AJ277607), Jena (AJO 11099), Leeds (AJ277608), Lordsdale (X86557), Melksham (X81879), Musgrove (AJ277614), Snow Mountain (AY134748), Southampton (L07418), Winchester (AJ277609) and Fayetteville (AY1 13106). Multiple alignments of deduced amino acid sequences of the capsid proteins were created by the Omiga v2.0 software (Oxford Molecular Ltd, Oxford, UK). Alignments were edited in GeneDoc v2.5. Dendrograms were constructed by the UPGMA clustering method of Molecular Evolutionary Genetics Analysis (MEGA version 2.1) with Poisson correction distance calculations and 125 bootstrap analyses.

Results:

A Broad Spectrum of Norovirus Binding Specificity to Human HBGAs

We describe herein seven (7) major HBGA Binding Patterns based on a study of 14 strains: VA387, GrV, Norwalk, C59, MxV, MOH, VA207, VA115, PiV, BUDS, Boxer, OIF, DSV, and HV (See FIGS. 1A-D and FIG. 4).

FIGS. 1A to 1D illustrate the binding of 14 noroviruses to saliva samples from individuals with different HBGA types. Saliva samples were tested at dilutions of 1:1000. The HBGA types of the individuals are shown in the bottom of the panels (Non-sec=Non-secretors; O=type O secretors; A=type A secretors; and B=type B secretors). As shown in FIG. 1A, the strains VA387 and GrV, representing a first binding pattern, can react with almost all secretor-related antigens containing the A, B and H epitopes. The A (or B) and the H epitopes are linked to the same galactose molecule with an α 1-3 and α 1-2 linkage, respectively, that are physically next to each other, suggesting that they are likely to act together. In contrast, Norwalk and C59, representing a second binding pattern, react with the A and H epitopes, but not the B epitope, indicating that there is specificity for binding a site on only the A epitope along with specificity for the H epitope.

Figure 1B:
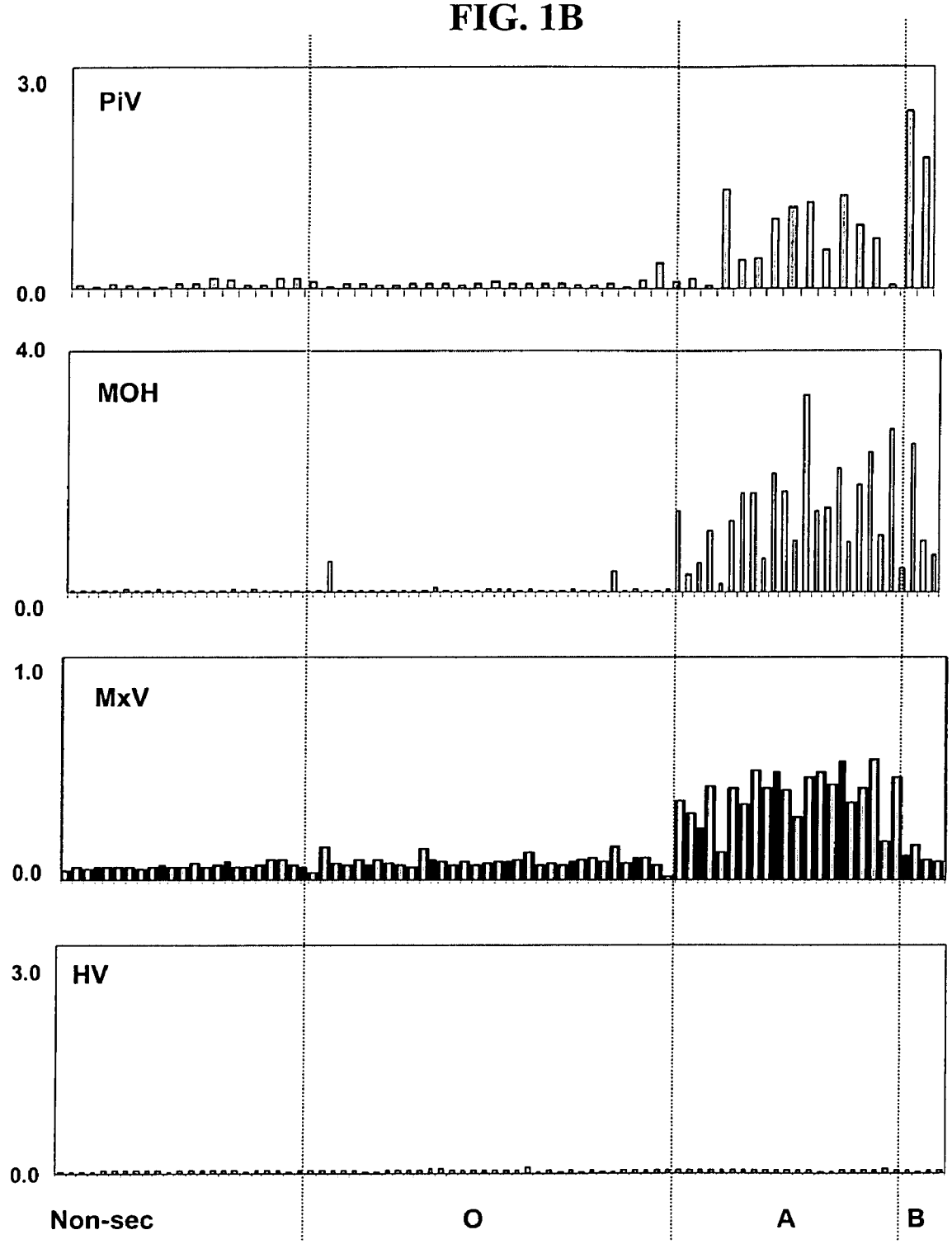
Figure 1C:
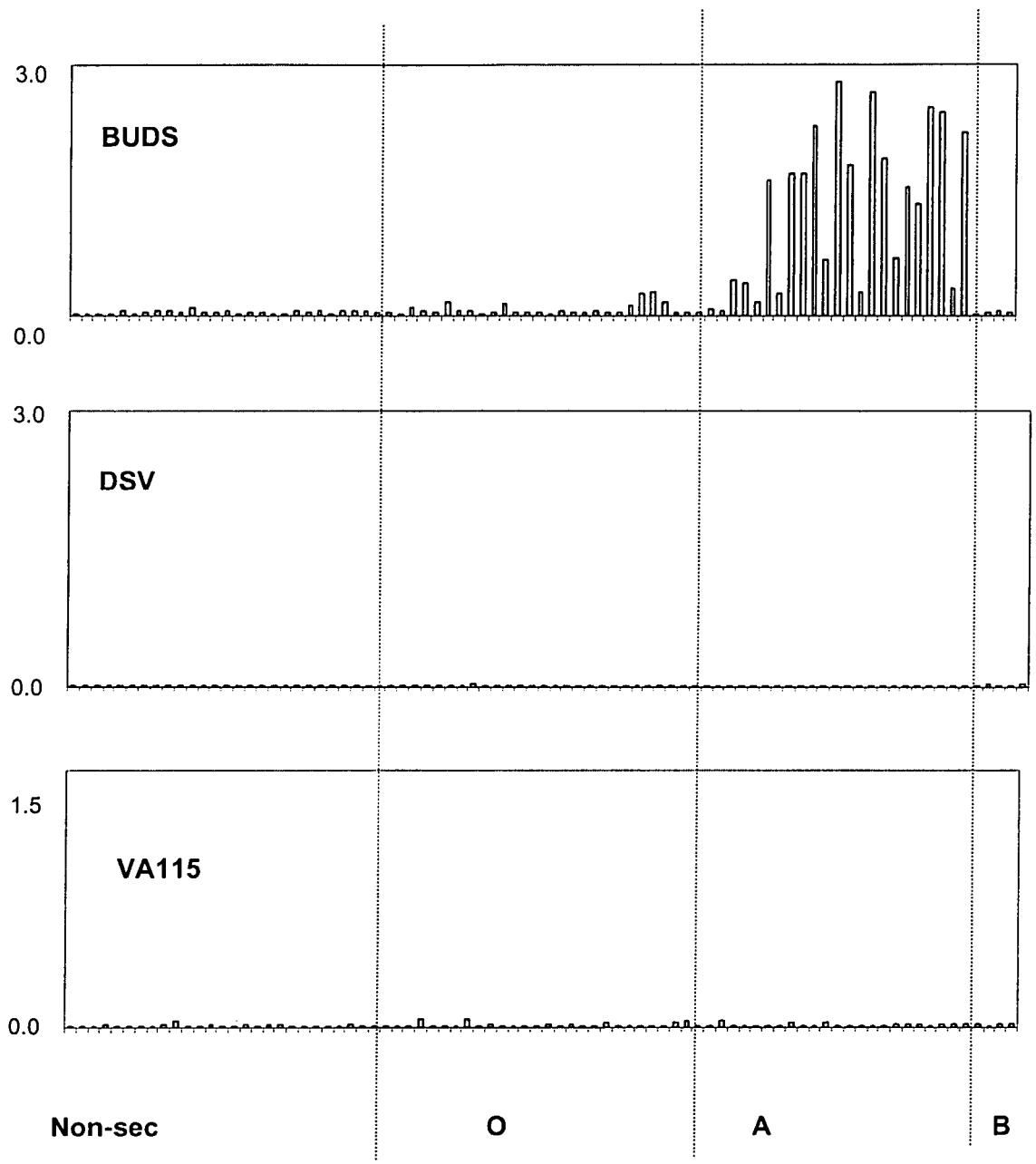

Looking at FIG. 1B, strains PiV, MOH and MxV, representing a third binding pattern, revealed nearly identical binding patterns, reacting with types A and B secretors but with little to no binding with type O secretors or non-secretors. In FIG. 1C, BUDS, representing a fourth binding pattern, revealed a similar binding pattern to PiV, MOH and MxV, but only recognizes saliva of type A secretors, not recognizing type B or O secretors or non-secretors. Strains DSV and VA115 did not react with any human HBGAs of the 81 saliva samples tested, even at a high concentration of both saliva (1:200 dilution) and VLPs (5 ug/mL), just as that of VA115. DSV is genetically close to VA115, which belongs to Genogroup I of noroviruses. As seen in FIG. 1B, HV also did not react with any human HBGAs; however, HV revealed significant binding with types A, B and Le$^b$ oligosaccharides, indicating it has a similar binding pattern to the third binding pattern of PiV, MOH, and MxV. None of the types A, B and Le$^b$ oligosaccharides reacted with DSV and VA115.

Figure 1D:
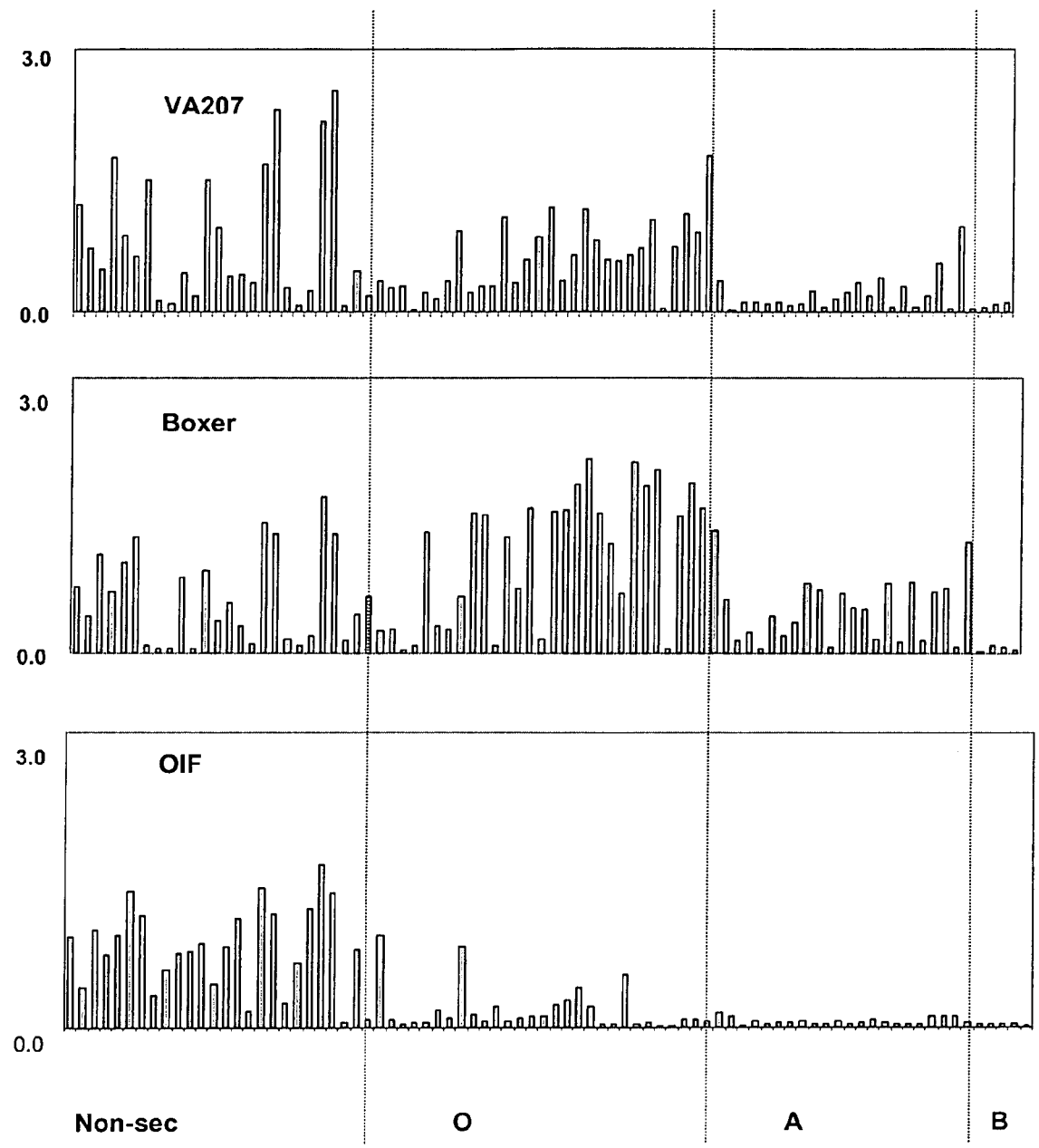

In FIG. 1D, Boxer and VA207 both show a similar binding pattern, both reacting with non-secretors, type O and type A secretors but not type B secretors. However, Boxer, representing a fifth binding pattern, had an equal or even higher binding activity to type O secretors than to non-secretors, compared to VA207. VA207 thus represents a sixth binding pattern. Strain OIF, representing a seventh binding pattern, bound saliva of non-secretors, with weak binding activity to type O secretors. In other studies using oligosaccharide- and MAb-based assays, significant differences in binding specificities to the Lewis and H epitopes were observed among the three non-secretor binding strains (VA207, Boxer and OIF).

Binding Specificity to Synthetic Oligosaccharides

Before each oligosaccharide was used, we performed a validation experiment to test its specificity using HBGA-specific MAbs. As summarized in Table B, thirteen oligosaccharide conjugates that contain the major ABH and Lewis epitopes were selected, along with another two oligosaccharide conjugates, H-1 and H-3 (trisaccharides), which either did not react with the corresponding MAb or did not have corresponding MAb available but reacted with norovirus VLPs. Most of the reactive oligosaccharide conjugates were highly specific to corresponding MAbs, although cross-reactions were observed in a few cases.

TABLE C: Synthetic HBGA oligosaccharide conjugates were coated to plate directly (BSA conjugates) or through streptavidin molecules (PAA-biotin conjugates). The binding of norovirus VLPs was detected by a pooled guinea pig hyperimmune antibody. The same scoring system described in Table B was used. di-=disaccharide, tri-=trisaccharide, tetra-=tetrasaccharide.

For example, Norwalk virus binds to saliva samples of types A and O secretors, but not type B secretors and non-secretors. Oligosaccharide-binding assays revealed that Norwalk virus reacted with the synthetic A but not B oligosaccharides, and it also reacted with $Le^b$, $Le^y$, H-1 and H-3,

TABLE B

Recognition of synthetic HBGA oligosaccharide conjugates by MAbs specific to HBGAs.

| Oligosaccharide conjugate | | $Le^a$ | $Le^b$ | $Le^x$ | $Le^y$ | H-1 | H-2 | Type A | Type B |
|---|---|---|---|---|---|---|---|---|---|
| PAA-biotin | $Le^a$ (tri-) | +++ | − | − | − | − | − | − | − |
| | $Le^b$ (tetra) | − | ++++ | − | − | − | − | − | − |
| | $Le^x$ (tri-) | − | − | ++ | − | − | − | − | − |
| | $Le^y$ (tetra) | − | − | − | ++++ | − | ++++ | − | − |
| | H-1 (tri-) | − | ++ | − | − | − | − | − | − |
| | H-2 (tri-) | − | − | − | − | − | ++++ | − | − |
| | H-3 (di) | − | − | − | − | − | − | − | − |
| | Type A (tri-) | − | − | − | − | − | − | ++++ | − |
| | Type B (tri-) | − | − | − | − | − | − | − | ++++ |
| BSA (Glycorex) | Type A | nd | nd | nd | nd | − | − | ++++ | − |
| | Type B | nd | nd | nd | nd | − | − | − | ++++ |
| BSA (V-Lab) | Type A | − | − | − | − | − | − | + | − |
| | Type B | − | − | − | − | − | − | − | ++++ |

TABLE B: Synthetic HBGA oligosaccharide conjugates were coated to plate directly (BSA conjugates) or through streptavidin molecules (PAA-biotin conjugates). The binding of MAbs was detected using a goat anti-mouse-HRP antibody. Reactivity was scored from strong (++++) to completely negative (−). Di=disaccharide, tri=trisaccharide, tetra=tetrasaccharide, nd=not done. (Glycorex and V-Lab are names of the sources of the oligosaccharide conjugates.)

Following the validation experiments, we performed oligosaccharide binding assays with norovirus VLPs representing variable binding patterns using the same conditions as the saliva binding assays. As summarized in Table C, most of the binding patterns obtained by the saliva binding assays were confirmed by the oligosaccharide binding assays.

which are expected HBGA products in the type O secretors. Corresponding results also were obtained for VA387 that reacted with most of the HBGA molecules, including types A, B, $Le^b$, $Le^y$, H-1 and H-3 that are expected products in the A, B, and O secretors. The finding that MOH reacted to types A and B but not to other oligosaccharides also confirmed the binding specificity of this strain that recognizes HBGAs in saliva of types A and B but not type O secretors.

The overall binding activities of the Lewis binding strains also agreed with our prediction. For example, as shown in Table C, OIF reacted with $Le^a$ only (non-secretors), VA207 reacted with $Le^x$ and $Le^y$ (in saliva experiments VA207 reacted with non-secretors, type O and type A secretors but not type B secretors), and Boxer reacted with $Le^b$ and $Le^y$, but none of them reacted with the A and B antigens.

TABLE C

Binding of synthetic HBGA oligosaccharide conjugates to norovirus VLPs.

| Oligosaccharide conjugate | Norovirus | | | | | | | | | |
|---|---|---|---|---|---|---|---|---|---|---|
| | A/B binding strains | | | | | | | Lewis binding strains | | |
| | VA387 | Norwalk | MxV | PiV | HV | MOH | BUDS | OIF | VA207 | Boxer |
| $Le^a$ (tri-) | − | − | − | − | − | − | − | + | − | − |
| $Le^b$ (tetra-) | ++ | ++ | + | + | + | − | − | − | − | ++ |
| $Le^x$ (tri-) | − | − | − | − | − | − | − | − | + | − |
| $Le^y$ (tetra-) | ++++ | + | − | − | − | − | − | − | +++ | ++ |
| H-1 (tri-) | + | +++ | − | − | − | − | − | − | − | − |
| H-2 (tri-) | − | − | − | − | − | − | − | − | − | − |
| H-3 (di-) | ++++ | + | − | − | − | − | − | − | − | − |
| A (tri-) | ++++ | +++ | ++ | + | + | +++ | +++ | − | − | − |
| B (tri-) | ++++ | − | ++ | ++ | ++ | +++ | +++ | − | − | − |

Not all Lewis binding strains reacted with all Lewis epitope-containing antigens ($Le^a$, $Le^b$, $Le^x$, or $Le^y$). In a subsequent study using MAbs to block binding, we also observed differences in binding to these epitopes among the three strains. Thus, the difference in reactions with the Lewis-containing oligosaccharides might be a reflection of strain-specific variations among these strains. More interestingly, the oligosaccharide-binding assays also detected binding activities that were not observed in the saliva-binding assays. For example, strain HV, which did not bind to any HBGAs in the saliva-binding assays, reacted with synthetic A, B and $Le^b$ antigens in the oligosaccharide-binding assays. Similarly, BUDS reacted with both synthetic A and B antigens in the oligosaccharide-binding assays (see Table C), while it bound only to type A saliva in the saliva-binding assays (see FIG. 1C). Furthermore, none of the PiV, MxV and HV VLPs bound to type O saliva in the saliva-binding assays (see FIG. 1B), but all three strains bound to synthetic $Le^b$ antigen in the oligosaccharide-binding assays (see Table C).

It was noted that all these binding activities were dose-related, but with a low OD value (below 1.0). In fact, the binding of HV to synthetic $Le^b$ also has been reported by others. Thus, we believe that these reactions are strain-specific and not an artifact. Possible reasons for the difference between results obtained by the saliva- and oligosaccharide-based assays are considered below.

The Lewis Binding Strains Recognize the Lewis Epitopes But Each May Have a Unique Binding Specificity Since the MAb-based assays have already confirmed the involvement of the Lewis epitopes in the binding of VA207, we performed additional blocking experiments on the three non-secretor binding strains (VA207, Boxer, and OIF) with MAbs against the four major Lewis epitope-containing antigens ($Le^a$, $Le^b$, $Le^x$, and $Le^y$). Table D provides the results of these blocking experiments.

TABLE D

Blocking of binding of VA207 and Boxer VLPs to saliva by monoclonal antibodies specific to HBGAs.

| Norovirus strain | Saliva type | Monoclonal antibody specific to | | | |
|---|---|---|---|---|---|
| | | $Le^a$ | $Le^b$ | $Le^x$ | $Le^y$ |
| VA207 | $Le^{a+x+}$ | +++ | – | +++ | – |
| | $Le^{b+y+}$ | – | +++ | – | +++ |
| Boxer | $Le^{a+x+}$ | – | – | – | – |
| | $Le^{b+y+}$ | – | +++ | – | +++ |
| OIF | $Le^{a+x+}$ | – | – | – | – |
| | $Le^{b+y+}$ | NA | NA | NA | NA |

TABLE D: Saliva samples with specific HBGA types were selected for coating the plate. For blocking, individual norovirus VLPs were pre-incubated with a MAb. Blocking activity was scored based on levels (++++, >90%; +++, 70-90%; ++, 50-70%; +, 30-50%, –, <30%.) of reduction of the OD values in wells with or without blocking MAbs. NA: not applicable.

Looking at Table D, MAbs against $Le^a$ and $Le^x$ strongly blocked VA207 binding to saliva containing $Le^a$ and $Le^x$ (non-secretor donors), as expected. However, they did not block Boxer and OIF binding to the same non-secretor saliva samples. MAbs against $Le^b$ and $Le^y$ blocked VA207 and Boxer binding to saliva containing $Le^b$ and $Le^y$ (secretor donors), but did not block their binding to saliva containing $Le^a$ and $Le^x$ (non-secretor donors). None of the four MAbs blocked OIF binding to saliva of non-secretors.

Thus, although the MAb-based assays did not confirm all results by the saliva and oligosaccharide assays, the fact that all three strains bound to saliva of the non-secretors indicates these strains are related by binding to the Lewis epitope (1,3/4 fucosyl residue). However, these strains are distinct, possibly by their variable affinity to the Lewis and H epitopes.

The A/B and H Epitopes Are Independent But Can Act Together In Binding to A/B Binding Strains Since most of the strains binding the A/B epitopes reacted with more than one epitope, we particularly studied the role of individual epitopes in association with other epitopes for binding VLPs. Specifically, as shown in both FIGS. 1A-D and Table C, the VA387-like strains (including VA387, Norwalk, GrV and C59) can react with almost all secretor-related antigens containing the A/B and H epitopes. The A/B and the H epitopes are linked to the same galactose molecule with an α 1-3 and α 1-2 linkage, respectively, that are physically next to each other, suggesting that they are likely to act together. To test this hypothesis, we performed blocking experiments using oligosaccharides or saliva as the blocking agents.

As shown in Tables E and F below, using oligosaccharides to block norovirus binding to oligosaccharides, we observed significant homologous blocking activities among oligosaccharide-conjugates containing the A, B and H epitopes. In addition, significant heterologous-blocking activities among different oligosaccharide conjugates have also been observed in strains of the A/B binding group. For example, as seen in Table E, the A and B antigens cross-blocked each other for their binding to VA387, as well as MOH and other MOH-like strains (BUDS, MxV and PiV; data not shown). As seen in Table F, the A and/or B trisaccharides also blocked the binding of VA387 and Norwalk virus to the H-containing antigens (H-1, H-3, $Le^b$ and $Le^y$), possibly at the common H recognition site of the capsids. Similarly, the H-containing antigens also blocked the binding of VA387 and Norwalk virus to the A and B antigens (trisaccharides) with variable efficiencies.

However, the Lewis epitopes ($Le^a$ and $Le^x$) did not block the binding of VA387, Norwalk virus, MOH or the "MOH-like strains" to the A/B and H epitopes, nor did the A and B trisaccharides block the binding of VA207, Boxer and OIF to the non-secretor saliva samples (data not shown).

TABLE E

Blocking of binding of norovirus VLPs to synthetic oligosaccharide conjugates by types A or B trisaccharide conjugates.

| Oligosaccharide-PAA-biotin | Norwalk virus | | VA387 | |
|---|---|---|---|---|
| | A (tri-) | B (tri-) | A (tri-) | B (tri-) |
| $Le^b$ (tetra-) | ++++ | – | ++++ | ++++ |
| $Le^y$ (tetra-) | +++ | – | ++++ | ++++ |
| H type 1 (tri-) | ++++ | – | NA | NA |
| H type 3 (di-) | +++ | – | ++++ | ++++ |
| A antigen | ++++ | – | ++++ | ++++ |
| B antigen | NA | NA | ++++ | ++++ |

TABLE E: Synthetic oligosaccharide PAA-biotin conjugates were coated to plate through streptavidin molecules. The binding of norovirus VLPs was detected by a pooled guinea pig hyperimmune antibody. For blocking, oligosaccharide conjugates (types A or B) were pre-incubated with norovirus VLPs before adding to the plates. The same scoring system described in Table D was used. di=disaccharide, tri=trisaccharide, tetra=tetrasaccharide, NA=not applicable. The binding of VA387 to H type 1 was weak, and oligosaccharide H type 1 was not included in the blocking study.

TABLE F

Blocking of binding of norovirus VLPs to types A or B trisaccharides conjugates by different synthetic oligosaccharide conjugates.

| Norovirus strain | Type A trisaccharide | | | | Type B trisaccharide | | | |
|---|---|---|---|---|---|---|---|---|
| | Le$^b$ | Le$^y$ | H-1 | H-3 | Le$^b$ | Le$^y$ | H-1 | H-3 |
| VA387 | ++ | +++ | – | +++ | ++ | +++ | – | +++ |
| Norwalk | ++ | – | ++ | + | NA | NA | NA | NA |
| MOH | – | – | – | – | – | – | – | – |
| MxV | – | – | – | – | – | – | – | – |
| BUDS | – | – | – | – | – | – | – | – |

TABLE F: synthetic oligosaccharide BSA conjugates (Types A or B) were coated to plate directly. The binding of norovirus VLPs was detected by a pooled guinea pig hyperimmune antibody. For blocking, oligosaccharide conjugates (Le$^b$, Le$^y$, H-1, or H-3) were pre-incubated with norovirus VLPs before adding to the plates. The same scoring system described in Table D was used. di=disaccharide, tri=trisaccharide, tetra=tetrasaccharide, NA=not applicable.

To further confirm these results, we also performed saliva-saliva blocking experiments using a panel of saliva samples representing different blood types for the coating and the blocking steps respectively.

Figure 2:
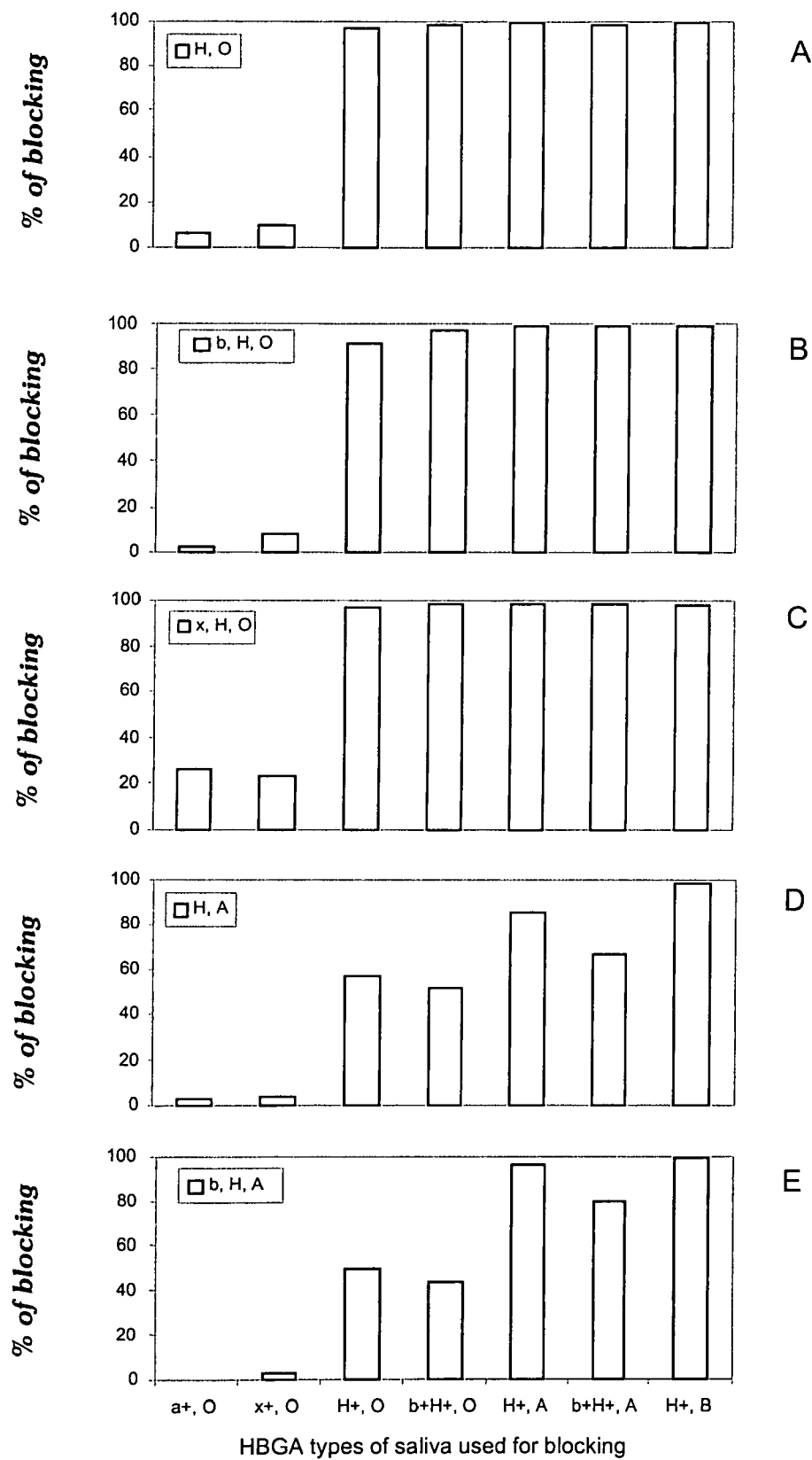
FIG. 2 shows graphic results for the blocking of VA387 binding to saliva by saliva.

FIG. 2 shows the typical results of the saliva blocking assays for VA387, binding to saliva by saliva. The standard saliva-binding assays were performed except for one additional step of pre-incubation of the VA387 VLPs with blocking saliva. Looking at FIG. 2, a set of five saliva samples with different HBGA types was used for the coating, as shown in panels A-E. Specifically, the saliva samples included type O, H positive in panel A; type O, Le$^b$ and H positive in panel B; type O, Le$^x$ and H positive in panel C; type A, H positive in panel D; and type A, Le$^b$ and H positive in panel E. For blocking, another set of seven saliva samples was used. The HBGA types of seven saliva samples are shown on the X axis (from left to right): type O, Le$^a$ positive (a+, O); type O, Le$^x$ positive (x+, O); type O, H antigen positive (H+, O); type O, Le$^b$ and H positive (b+H+, O); type A, H positive (H+, A); type A, Le$^b$ and H positive (b+H+, A) and type B, H positive (H+, B). The levels of blocking (%) of the binding were calculated by the OD values between wells with or without pre-incubation with a saliva sample. The original OD values of VA387 to the five saliva samples without blocking were >3.0.

Summarizing FIG. 2, the following conclusions can be made: (1) significant blocking of binding were observed among homologous blood types, (2) significant heterologous blocking activities were also observed among secretor saliva (types A, B and O), (3) saliva of non-secretors did not block the binding to the A, B and H antigens, and (4) saliva samples with more complex antigens (e.g. types A and B secretors) were stronger blockers than saliva samples with less complex antigens (e.g. type O secretors).

Thus, both A/B and H are independent epitopes but they can act together depending on the structure of the binding interface of norovirus capsids. Strains MOH and BUDS apparently have one binding site to the A/B epitopes, while the remaining strains of the A/B binding group may contain two sites within the binding interface. The A and B epitopes may share the same binding site for the majority of the A/B binding group, except for Norwalk and C59 that only recognize the A but not B antigens. The H epitope is associated with the A/B epitopes in the binding, but it can act alone in the type O secretors. The fact that the A/B and Lewis epitopes do not cross-block each other indicates that strains in these two groups have distinct binding interfaces on the viral capsids. Strains with Similar Binding Patterns Tend To Be Genetically Clustered The finding that the A/B binding group and the Lewis binding group mutually exclude the A/B or Lewis epitopes raised a possibility that the human HBGAs may play a role in norovirus evolution. However, we did not observe a clear segregation of the two binding groups with the genogroups of noroviruses when the entire capsid sequences were analyzed. In a recent study, we demonstrated that the P domain is responsible for and contains the essential elements for the binding of norovirus VLPs to HBGAs. Therefore, we performed a phylogenetic analysis focusing on the P domain, but still no genetic correlation was observed between the two binding groups (data not shown).

Figure 3:
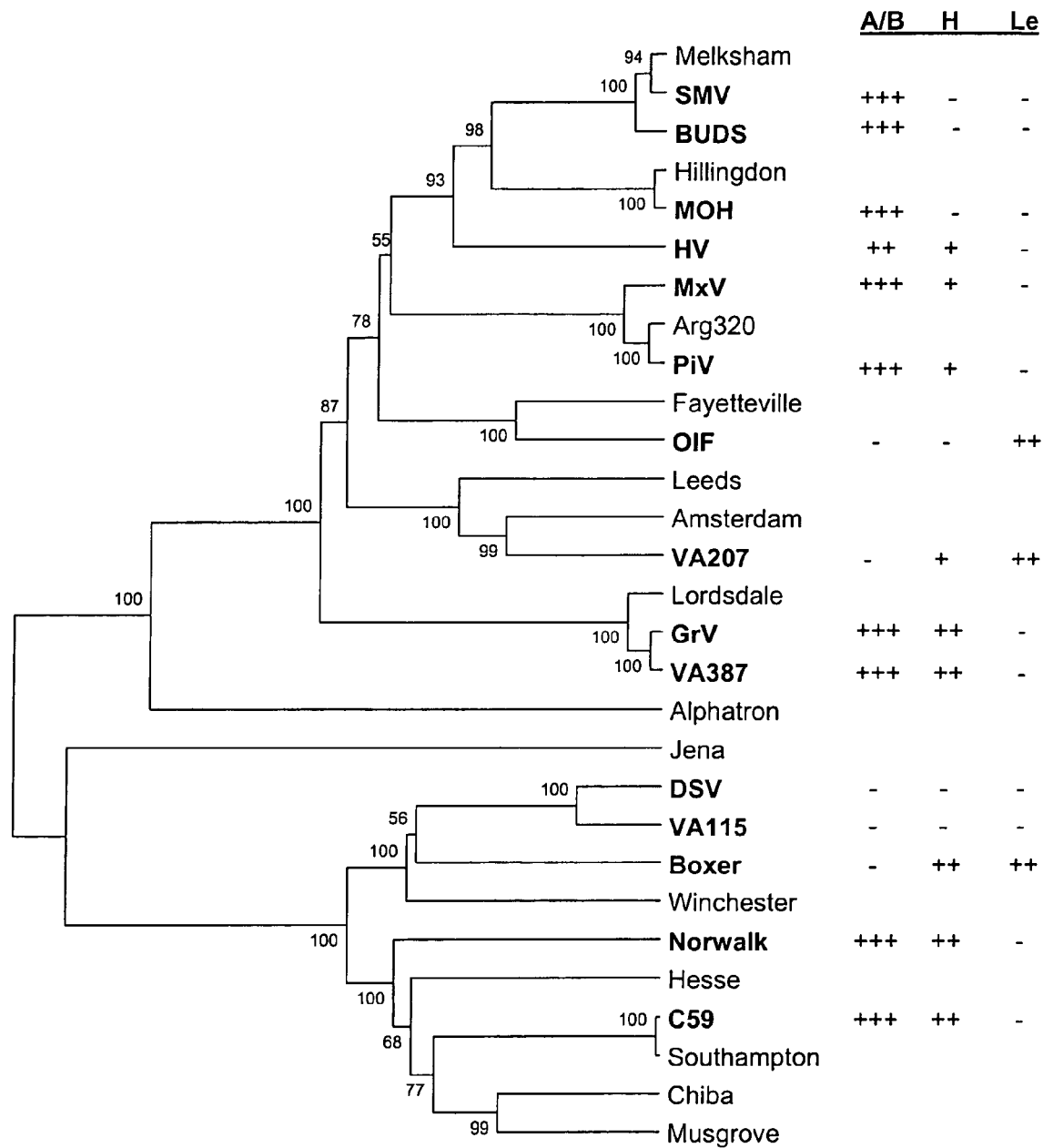
FIG. 3 illustrates the phylogenetic tree and prediction of HBGA targets of noroviruses determined by binding and blocking experiments.

However, FIG. 3 illustrates phylogenetic tree and prediction of HBGA targets of noroviruses determined by binding and blocking experiments. The phylogenetic tree was constructed based on the amino acid sequences of the entire capsid genes using the UPGMA clustering method (MEGA v2.1) with Poisson correction distance calculations. Scale bar represents the phylogenetic distances expressed as units of expected amino acid substitutions per site. The numbers on each branch indicate the bootstrap values for the genotype. Bootstrap values are indicated as % of 125 replicates. Strains characterized in this study are in bold. Strain SMV was characterized by Harrington et al. based on oligosaccharide binding assays. The potential HBGA targets for individual strains are shown on the right panel. The binding results of each strain were assigned based on reactions in assays with saliva and/or oligosaccharide conjugates. "+" indicates a positive binding observed in any of the assays, "++, +++" indicate higher binding signals, and "–" indicates no binding.

Looking at FIG. 3, when the 14 strains were listed on a phylogenetic tree in relation to their binding patterns, clear relationships of genetic identities with binding patterns were observed among some strains. For example, GrV and VA387 are the only two strains that bound types A, B and O secretors and both belong to the same cluster (G114) of genogroup II that share overall 98% of amino acid sequence identity. Norwalk virus and C59 are two strains that bound to the A and O, but not B, secretors and they are genetically close to each other. In addition, both BUDS and MOH bound only the A/B epitopes and they are more related to each other than to any other strains studied. Furthermore, HV, MxV, and PiV revealed similar binding patterns to the A/B and H antigens, and they are related with the shortest phylogenetic distances to each others. Finally, strains VA115 and DSV are the only two strains that did not react with any HBGAs and they are genetically close to each other.

Thus, the strain specificities are genetically related, indicating that human HBGAs are involved in norovirus evolution. However, the scattering of strains of the two binding groups in both genogroups indicates other factor(s) may also be involved in norovirus evolution.

The present invention has significantly extended the understanding of the diversity of norovirus/HBGA interaction by characterization of 14 strains representing 13 genetic clusters of noroviruses. Seven Binding Patterns have been identified based on the saliva-, MAb- and oligosaccharide-based assays according to the interaction with three major epitopes (A/B, H and Lewis) of HBGAs. According to the blood types of the saliva donors, the seven Binding Patterns can be classified into two groups: (1) the A/B binding group (Norwalk, C59, VA387, GrV, MOH, PiV, MxV, HV and BUDS); and (2) the Lewis (non-secretor) binding group (VA207, Boxer and OIF).

As illustrated in FIGS. 1A-1D, all strains in the A/B binding group bound to types A and/or B and O (H epitope) saliva of secretors but not to saliva of non-secretors, while all strains in the Lewis binding group bound to saliva of non-secretors and type O secretors but with weak binding or no binding to the types A and B secretors.

Figure 4:
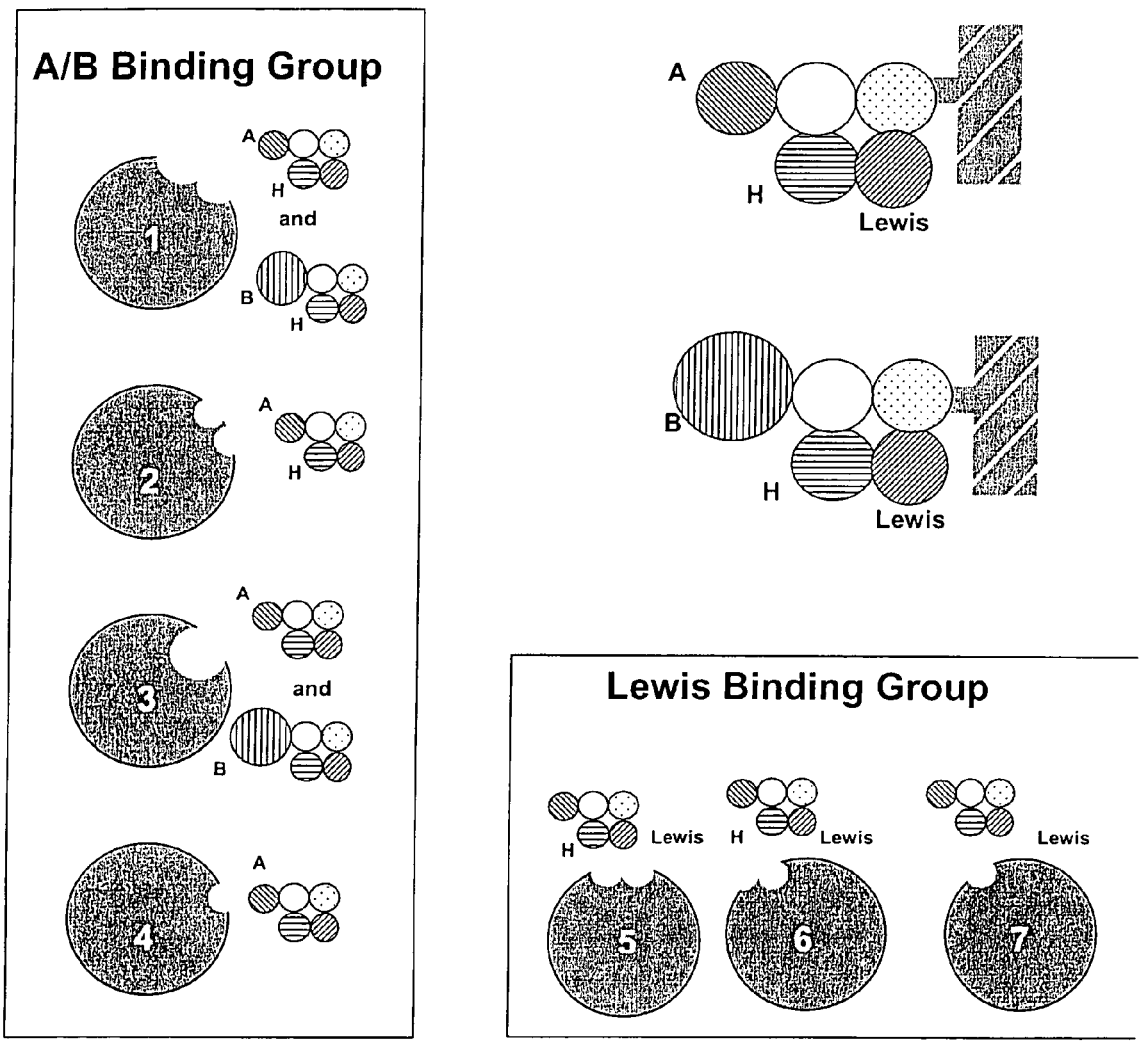
FIG. 4 illustrates a model of the seven Binding Patterns of norovirus/HBGA interaction, which are further divided into two binding groups, the "A/B, H binding group" and the "Lewis binding group."

Based on FIGS. 1A-1D, seven Binding Patterns emerge as being significant. Two groups, (A) the A/B, H binding group; and (B) the Lewis binding group, include the seven Binding Patterns, which are listed here:

(A) A/B, H binding group:
1. Binds A, B, and H epitopes: VA387, GrV
2. Binds A and H epitopes: Norwalk, C59
3. Binds A and B epitopes: PiV, MxV, HV, MOH
4. Binds A epitope: BUDS (B) Lewis binding group:
5. Binds non-secretors (Lewis epitope) with strong affinity to H epitope: Boxer
6. Binds non-secretors (Lewis epitope) with weak affinity to H epitope: VA207
7. Binds only non-secretors (Lewis epitope): OIF Based on this grouping, FIG. 4 illustrates a proposed model of the norovirus/HBGA interaction. This model was developed based on the classification of the two binding groups of norovirus to human HBGAs, (A) the A/B, H binding group; and (B) the Lewis binding group. The pair of five-circle structures shown on the top-right corner of FIG. 4 represents pentasaccharides as the final product (ALe$^b$ or BLe$^b$) of the human HBGAs. Twelve norovirus strains are represented by the seven Binding Patterns listed as 1 through 7 in FIG. 4, according to their relative interaction levels with the A epitope (the circular structure indicated by forward slash lines), the B epitope (for convenience shown as a larger circular structure than the A epitope and indicated by vertical lines), the H epitope (indicated by horizontal lines), and the Lewis epitope (indicated by backward slash lines). The clear circular structure represents a galactose molecule to which the A, B and H epitopes are bound, and the stippled circular structure represents GlcNAc.

Specifically, looking at FIG. 4, the seven Binding Patterns are listed below as BP #'s 1 through 7, followed by their respective binding sites and norovirus strains:
1. Binding Pattern (BP) #1: norovirus strains that bind A or B, and H epitopes: VA387, GrV
2. BP #2: norovirus strains that bind A and H epitopes: Norwalk, C59
3. BP #3: norovirus strains that bind A or B epitopes only: PiV, MxV, HV, MOH
4. BP #4: norovirus strains that bind A epitope only (based on the saliva binding assays): BUDS
5. BP #5: norovirus strains that bind non-secretors (Lewis epitope) with strong affinity to H epitope: Boxer
6. BP #6: norovirus strains that bind non-secretors (Lewis epitope) with weak affinity to H epitope: VA207
7. BP #7: norovirus strains that bind only non-secretors (Lewis epitope): OIF Still looking at FIG. 4, the potential binding sites for each of the four HBGA epitopes (notably A, B, H, and Lewis) on the capsid are indicated. One can also refer to FIGS. 1A-D to review the interaction level of each binding pattern. In general, each strain has one binding interface that can accommodate at least one of the four major epitopes of HBGAs (A, B, H or Lewis). Binding activities with one or a combination of two of the three sugar side chains determine the binding patterns of the strains. The combinations of affinities to the A, B and/or H epitopes determine the binding patterns of the strains of the A/B binding group, while the combinations of the affinities to the Lewis and/or H epitopes determine the binding patterns of strains in the Lewis binding group.

Thus, as shown in FIG. 4, strains in each binding group can be further divided according to their combined binding activities to corresponding epitopes. According to this model, the complicated binding results observed can be easily explained. For example, strains VA387 and GrV represent binding pattern 1 and have a strong affinity to either [A and H] or [B and H], therefore they bound strongly to types A, B and O saliva. Norwalk virus and C59 represent binding pattern 2 and recognize A and H, but not B. Strains PiV, MxV, Hawaii and MOH represent binding pattern 3 and have a strong affinity to either A or B, and also have a relatively weak affinity to H, such they reacted strongly with the A and B antigens but weakly with the H epitope-containing antigen (FIG. 1A). BUDS represents binding pattern 4 and has only one site, for the A epitope, and correspondingly binds to the A secretors only (FIG. 1C).

As shown in the Lewis binding group at FIG. 4, Boxer represents binding pattern 5 and has a strong affinity to both H and Lewis epitopes, VA207 represents binding pattern 6 and has a strong affinity to the Lewis epitope and a weak affinity to the H epitope, while OIF represents binding pattern 7 and only recognizes the Lewis epitope. In other words, while all three strains in the Lewis binding group may recognize the Lewis epitope, the addition of an α 1,2-linked fucose (H epitope) significantly increases the affinity of Boxer (binding pattern 5) to the Lewis epitope, while this effect was less for VA207 (binding pattern 6) and the least for OIF (binding pattern 7).

Furthermore, the addition of the A and B epitopes may have a negative effect (epitope masking) on the binding to the Lewis and/or H epitopes for these strains. Therefore, as shown in FIG. 1B, VA207 revealed a typical "three-step-interaction" pattern that has the strongest binding activities with saliva of the non-secretors, intermediate binding activities with saliva of the type O secretors, and the lowest binding activities with saliva of the types A and B secretors. The "masking effect" of the B epitope probably is stronger, as none of the three strains bound saliva of type B secretors. The predicted affinity of Boxer and OIF also can be seen clearly in the saliva binding assays of FIG. 1B, in which Boxer had a stronger binding activity to the type O secretors than to the non-secretors, and OIF did not bind, or bound weakly, to the type O secretors.

The inconsistent results obtained from the saliva- and the oligosaccharide-based binding assays may be due to some subtle differences between the synthetic products made in vitro and the authentic antigens found in vivo. As observed in our validation experiments, many factors on the oligosaccharide determinants, the carriers and the spacers of the conjugates, can affect the affinity (data not shown). In addition, the layout or presentation of the HBGAs also may be different between the in vitro and in vivo conditions. HBGAs are likely to be presented on mucin or mucin-like molecules with a special array and density of the antigens which may not be the same under the conditions of the synthetic products. Because the norovirus/HBGA interaction is a typical protein/carbohydrate interaction, like the lectin/carbohydrate interaction that is highly diverse, a subtle change of the binding interface of the antigens could result in binding pattern change of the strains. Noroviruses are genetically highly diverse, and a single amino acid change of the P domain of the viral capsid protein can result in HBGA binding pattern changes.

Thus, noroviruses could have a wide spectrum of binding specificities to HBGAs due to their wide genetic diversity. This is also true for MAbs, because MAb/HBGA interaction also is a typical protein/carbohydrate interaction. Therefore, it is not surprising when incongruous results are obtained between different assays with different reagents and among norovirus strains, because each of them could have subtle differences in HBGA recognition. The lack of interaction of the H-1 trisaccharide to the H-1 MAb observed in our study could be another example possibly due to different sources of these reagents.

Although variable results have been observed among different assays and different reagents, the cross-blocking experiments using the same types of reagents were highly consistent. One significant finding of the present invention is that different HBGAs containing shared epitopes can cross-block each other for binding to different noroviruses. This finding not only confirmed the single binding pocket hypothesis, but also provides a useful strategy to develop antiviral drugs against noroviruses. As demonstrated in the cross-blocking experiments, the trisaccharide A and B antigens were able to block all A/B and H antigen related binding.

Thus, using the information provided by these studies, it is possible to develop a single oligosaccharide molecule to block the binding of most norovirus strains in A/B binding group and partially block some strains in Lewis binding group to HBGAs. The finding that more complex HBGAs are more capable of blocking is particularly useful for designing such molecules as antivirals for NV. Theoretically, oligosaccharides such as the types A and B pentasaccharides (ALe$^b$ and BLe$^b$) that contain the A, B, H and Lewis epitopes would be the ideal antiviral compounds for their potential blocking activities. Due to the possible masking effect of the A/B epitope, additional molecules containing the H and/or Lewis epitopes only also may be included.

EXAMPLES

Example 1

A test was conducted to measure the binding by one or more recombinant noroviruses with blood antigens in human saliva samples.

Human subject phenotypes: The human subjects' phenotypes of histo-blood group antigens were determined by EIAs using monoclonal antibodies specific to Le$^a$, Le$^b$, A, B and H blood group antigens. Salivary anti-norovirus IgA was determined by EIAs using recombinant norovirus capsids as coating antigens.

Saliva samples were diluted at 1: 1,000 in PBS and then coated onto microtiter plates (Dynex Immulon) overnight at 4° C. After blocking with 5% Blotto, monoclonal antibodies specific to Lewis a, Lewis b, H type 1, type A, and type B antigens were added. MAbs BG-4 anti-H type 1, BG-5 anti-Le$^a$, and BG-6 anti-Le$^b$ were purchased from Signet Pathology Systems (Dedham, Mass.). MAbs BCR9031 anti-H type 2, BCR 9010 anti-A, and BCRM 11007 anti-B were purchased from Accurate Chemical & Scientific Corporation (Westbury, N.Y.). After incubation for 1 hour at 37° C., HRP-conjugated goat anti-mouse IgG or IgM antibodies were added. Following each step, the plates were washed 5 times with PBS. The color reaction was developed and recorded as described above.

Of the 54 human subjects, 11 (20%) were Le$^+$/non-secretors, 36 (67%) were Le$^+$/secretors, and 7 (13%) were Le$^-$ individuals. Among the 7 Le$^-$ individuals, 6 were secretors and one was a non-secretor. Of the 54 individuals, 17 (32%) were type A, 4 (7%) were type B, 33 (61%) were type O, and none were type AB.

Recombinant norovirus capsid: Baculovirus-expressed recombinant capsid proteins of five norovirus strains were prepared by methods disclosed in the art: one virus of genogroup I norovirus strains (NV) and three viruses of genogroup II norovirus strains (strains 207, 387, 02-1419, and MOH).

Procedure: The recombinant viral capsid protein of each of the five norovirus strains was tested by enzyme immune assays (EIAs) for the ability to bind to blood antigens in saliva samples of each human subject. The saliva samples were boiled and centrifuged, and the supernatant stored frozen until use. For testing recombinant norovirus (rNLV) binding to saliva, microtiter plates (Dynex Immulon, Dynatech) were coated with the saliva samples at a dilution of 1:5,000 in phosphate buffer saline (PBS). After blocking in 5% dried milk (Blotto), the rNLV capsid proteins at ~1.0 µg/ml in PBS were added. The bound rNLV capsid proteins were detected using a pooled guinea pig anti-noroviruss antiserum for the respective NOROVIRUS, followed by addition of horseradish peroxidase (HRP)-conjugated goat anti-guinea pig IgG (ICN, Aurora, Ohio). In each step, the plates were incubated for 1 hour at 37° C. and washed five times with PBS. The enzyme signals were detected by the TMB kit (Kirkegard & Perry Laboratories, Gaithersburg, Md.) then read at a wavelength of 450 nm using an EIA spectra reader (Tecan, Durham, N.C.) as described by the manufacturers.

Figure 5:
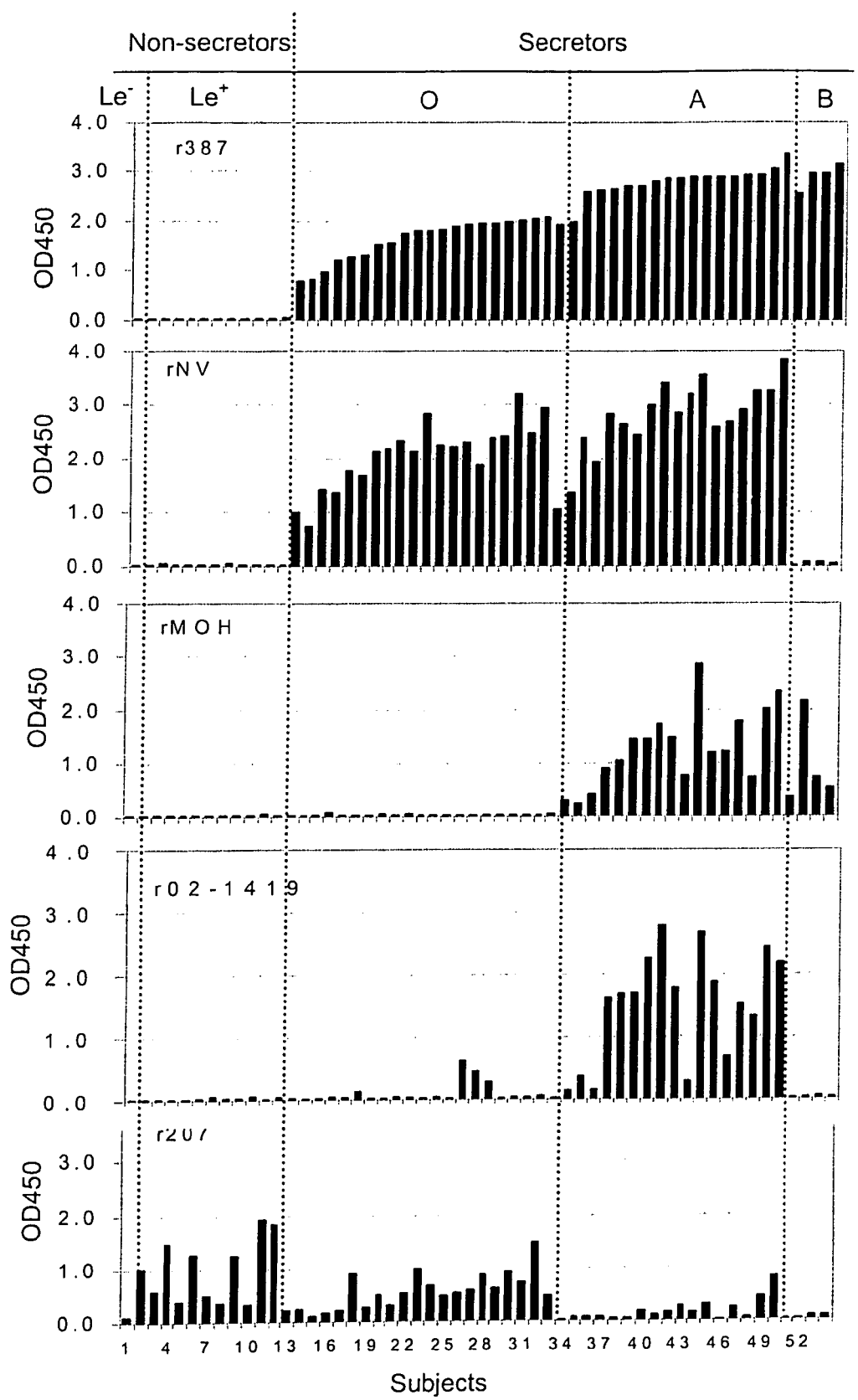
FIG. 5 shows graphic results of the binding strength of five NLVs based on histo-blood phenotype of Lewis negative ($Le^-$) secretors (A, B and O blood types) and non-secretors.
Figure 6:
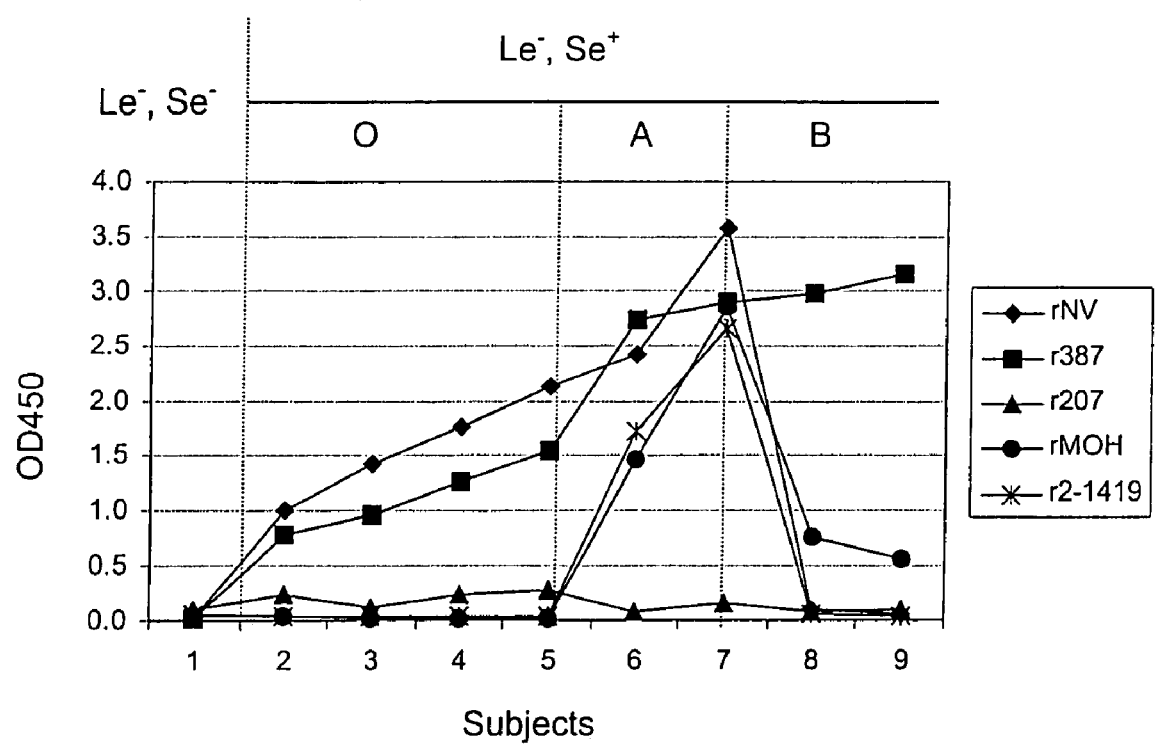
FIG. 6 shows graphic results of the binding strength of five NLVs based on histo-blood phenotype of Lewis negative ($Le^-$) secretors (A, B and O blood types) and non-secretors.

The results are shown in FIG. 5, which is a graphic representation of the binding strength of the five norovirus strains based for 9 Lewis negative (Le$^-$) subjects with HBGA phenotypes secretors (A, B and O blood types) and non-secretor. FIG. 6 shows graphic results of the binding strength of the five NLVs based for the 9 Lewis negative (Le$^-$) subjects with histo-blood phenotypes secretors (A, B, and O blood types) and non-sector. Without being bound to any particular theory, these results and the known biosynthetic pathways for human histo-blood group antigens show that certain virus strains appear to recognize specific determinant epitopes on the histo-blood group antigens. Strain 207 apparently recognizes Le$^a$ antigen, as Le$^a$ is the only antigen found in the saliva of Lewis-positive non-secretor individuals. Secretor individuals also can make Le$^a$ antigens, although at smaller amounts in saliva as compared to other blood antigens, due to the presence of 1,2 fucosyltransferase expressed by the secretor gene (FUT2). Thus 207 virus binds at minimal levels and with less avidity to the saliva of secretors than to non-secretors. Variable expression of the FUT2 fucosyltransferase in secretors may account for the lack of a clear demarcation between 207 binders and non-binders. Strain 207 did not bind to blood antigens in the saliva from Lewis-negative individuals who lack FUT3 and thus do not make Le$^a$ antigen. VA207 also recognizes Le$^x$ that is the product of the FUT3 enzyme on the type 2 molecules.

The histo-blood group antigens in the saliva of secretor individuals are more complex due to the interactions between the ABO, Lewis, and secretor genes. Strain 387 has a broad specificity, possibly binding all fucosylated antigens in secretors; similarly, NV binds all fucosylated antigens except for type B. MOH is predicted to recognize type A and type B antigens but not H and Le$^b$ antigens, because MOH reacted with types A and B but not with type O. Strain 02-1419 appears to bind type A antigen, but not the H, B, Le$^b$ and Le$^a$ antigens, because 02-1419 strain reacted with type A but not with types B or O. These four secretor-binding strains also recognize H type 2, Le$^y$, A type 2 and B type 2, A Le$^y$, and B Le$^y$, because these are the product of the FUT2 enzyme on the type 2 molecules. The Lewis epitope, i.e., moieties containing α1,4 fucose in Lewis-positive secretors, does not appear important for binding by MOH, 387, NV, and $O_2$-1419, because these strains bind to saliva from Lewis-negative secretors, who lack this epitope. The presence of the Lewis epitope did not affect viral binding to other epitopes; therefore, the antigens in secretor individuals that bind MOH, 387, 02-1419, or NV are probably limited to the H, A, and B antigens.

Example 2

A test was conducted to demonstrate that the binding of a norovirus to a blood antigen in its natural binding pattern is inhibited and prevented by contacting the norovirus with a compound known to bind to the determinant binding site in the norovirus capsid. The Norwalk Virus (NV) is known to bind with the H antigen and the A antigen (that is, these antigens are in its binding pattern). Recombinant NV capsid protein at ~1.0 μg/ml in PBS was coated into the well(s) of a microtiter plate (Dynex Immulon, Dynatech). After blocking, a MAb 9C3, known to bind to the determinant binding site of the NV, was applied to a first group of the NV targets. A second group of the NV targets were left untreated. After incubation, the first set of NV targets was washed five times with PBS. Saliva from a person of secretor-A phenotype was prepared as in Example 1, and applied to both the first and second groups of NV targets. After incubation, both groups of NV targets were detected with an A-antigen antibody to detect the presence of A antigen on the NV targets. The first group of NV targets showed no A antigen, while the second group of NV targets showed significant A antigen from the saliva sample binding to the norovirus.

The research described in the present invention was supported by the United States National Institutes of Health (National Institute of Allergy and Infectious Diseases), RO1 A137093-7, and National Institute of Child Health and Human Development. While the present invention has been illustrated by the description of embodiments and examples thereof, it is not intended to restrict or in any way limit the scope of the appended claims to such detail. Additional advantages and modifications will be readily apparent to those skilled in the art. Accordingly, departures may be made from such details without departing from the scope or spirit of the invention.

What is claimed is:

1. A kit for determining whether an individual has been infected by a norovirus, comprising:
    a) at least one container for receiving a stool sample from an individual suspected of being infected by a norovirus, the at least one container comprising a solid media support having been affixed with at least two different histo-blood group antigens selected from the group consisting of H antigen, A antigen, B antigen, $Le^b$ antigen, and $Le^a$ antigen, the at least two different histo-blood group antigens being capable of complexing with the norovirus; and
    b) at least one detectable anti-norovirus antibody that binds to a non-determinant epitope of the norovirus of the norovirus-histo-blood group antigen complex.

2. The kit according to claim 1, wherein the at least one detectable anti-norovirus antibody comprises a plurality of the at least one detectable anti-norovirus antibodies.

3. The kit according to claim 1, wherein the kit further comprises a washing media for washing away unbound stool sample.

4. The kit according to claim 1, wherein the solid media support has been affixed with at least three different histo-blood group antigens.

5. The kit according to claim 4, wherein the solid media support has been affixed with at least four different histo-blood group antigens.

6. A kit for determining if a food or water is contaminated by a norovirus, or if an individual has been infected by a norovirus, comprising:
    a) at least one container for receiving a sample of the food or water suspected of being contaminated by the norovirus, or a biological sample from an individual suspected of being infected by the norovirus, the at least one container comprising a solid media support having been affixed with at least two different histo-blood group antigens selected from the group consisting of H antigen, A antigen, B antigen, $Le^b$ antigen, and $Le^a$ antigen, the at least two different histo-blood group antigens being capable of complexing with the norovirus; and
    b) at least one detectable anti-norovirus antibody that binds to a non-determinant epitope of the norovirus of the norovirus-histo-blood group antigen complex.

7. The kit according to claim 6, wherein the at least one detectable anti-norovirus antibody comprises a plurality of the at least one detectable anti-norovirus antibodies.

8. The kit according to claim 6, wherein the kit further comprises a washing media for washing away unbound biological sample.

9. The kit according to claim 1 further comprising at least two different anti-antigen antibodies that bind to the antigen-determinant epitope of a respective one or the other of the at least two histo-blood group antigens.

10. The kit according to claim 1 where the at least two different histo-blood group antigens includes at least the H antigen, the A antigen, and the B antigen.

11. The kit according to claim 1 where the at least two different histo-blood group antigens includes at least the H antigen, the A antigen, the B antigen, the $Le^b$ antigen, and the $Le^a$ antigen.

12. The kit according to claim 1 wherein the at least two different histo-blood group antigens are affixed to the solid media support as distinct targets.

13. The kit according to claim 6, wherein the biological sample is selected from the group consisting of a tissue sample selected from the group consisting of blood, vascular endothelial cells, intestinal epithelial cells, cervical epithelial cells, urothelial epithelial cells, pulmonary epithelial cells, and mammary epithelial cells, and a body fluid sample selected from the group consisting of saliva, breast milk, urine, and feces.

14. The kit according to claim 6 further comprising at least two different anti-antigen antibodies that bind to the antigen-determinant epitope of a respective one or the other of the at least two histo-blood group antigens.

15. The kit according to claim 6 where the at least two different histo-blood group antigens includes at least the H antigen, the A antigen, and the B antigen.

16. The kit according to claim 6 where the at least two different histo-blood group antigens includes at least the H antigen, the A antigen, the B antigen, the $Le^b$ antigen, and the $Le^a$ antigen.

17. The kit according to claim 6 wherein the at least two different histo-blood group antigens are affixed to the solid media support as distinct targets.

* * * * *

UNITED STATES PATENT AND TRADEMARK OFFICE
CERTIFICATE OF CORRECTION

PATENT NO. : 7,977,098 B2  
APPLICATION NO. : 11/264992  
DATED : July 12, 2011  
INVENTOR(S) : Xi Jiang et al.

It is certified that error appears in the above-identified patent and that said Letters Patent is hereby corrected as shown below:

In the Specification:

Column 1, lines 18-23 should read

-- INTERESTS

This invention was made with government support under HD013021 and AI037093 awarded by the National Institutes of Health. The government has certain rights in the invention. --

Signed and Sealed this  
Twenty-fifth Day of June, 2013

Teresa Stanek Rea  
*Acting Director of the United States Patent and Trademark Office*